United States Patent
Chan et al.

(10) Patent No.: US 7,824,395 B2
(45) Date of Patent: Nov. 2, 2010

(54) METHOD AND APPARATUS FOR MONITORING AND CONTROLLING THERMALLY INDUCED TISSUE TREATMENT

(75) Inventors: Kin F. Chan, San Jose, CA (US);
George Frangineas, Fremont, CA (US);
Leonard C. DeBenedictis, Palo Alto, CA (US); Robert Kehl Sink, Mountain View, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 1035 days.

(21) Appl. No.: 11/468,275

(22) Filed: Aug. 29, 2006

(65) Prior Publication Data

US 2007/0093797 A1 Apr. 26, 2007

Related U.S. Application Data

(60) Provisional application No. 60/712,358, filed on Aug. 29, 2005.

(51) Int. Cl.
*A61B 18/18* (2006.01)
(52) U.S. Cl. .................. 606/10; 606/9; 606/12; 607/88; 607/89; 128/898
(58) Field of Classification Search ............... 606/2–19; 607/88–94; 128/898
See application file for complete search history.

(56) References Cited

U.S. PATENT DOCUMENTS

| | | |
|---|---|---|
| 4,556,057 A | 12/1985 | Hiruma et al. |
| 4,587,396 A | 5/1986 | Rubin |
| 4,613,866 A | 9/1986 | Blood |
| 4,641,650 A | 2/1987 | Mok |
| 4,737,794 A | 4/1988 | Jones |
| 4,741,612 A | 5/1988 | Birngruber et al. |

(Continued)

FOREIGN PATENT DOCUMENTS

EP 1433430 A2 6/2004

(Continued)

OTHER PUBLICATIONS

PCT International Search Report and Written Opinion, PCT/US2008/061067, Oct. 3, 2008, 10 pages.

(Continued)

*Primary Examiner*—Ahmed M Farah
(74) *Attorney, Agent, or Firm*—Wood, Herron & Evans, LLP

(57) ABSTRACT

A method and apparatus for thermal treatment of tissue by irradiating the skin with electromagnetic energy is disclosed. Sources of electromagnetic energy include radio frequency (RF) generators, lasers, and flashlamps. The apparatus includes either a positional sensor or a dosage evaluation sensor, or both types of sensors. These sensors provide feedback to a controller. The controller may control the electromagnetic source parameters, the electromagnetic source activation, and/or the sensor measurement parameters. An additional scanning delivery unit may be operably coupled to the controller or to the sensors to provide a controlled distribution of electromagnetic energy to the target region of the skin. The use of positional measurement sensors and dosage evaluation sensors permits the controller to automatically determine the proper electromagnetic source parameters including, for example, pulse timing and pulse frequency.

20 Claims, 11 Drawing Sheets

U.S. PATENT DOCUMENTS

| | | | |
|---|---|---|---|
| 4,742,356 A | 5/1988 | Kuipers | |
| 4,813,412 A | 3/1989 | Yamazaki et al. | |
| 4,973,848 A | 11/1990 | Kolobanov et al. | |
| 4,974,587 A | 12/1990 | Turner et al. | |
| 5,057,099 A | 10/1991 | Rink | |
| 5,106,387 A | 4/1992 | Kittrell et al. | |
| 5,178,617 A | 1/1993 | Kuizenga et al. | |
| 5,307,072 A | 4/1994 | Jones, Jr. | |
| 5,312,396 A | 5/1994 | Feld et al. | |
| 5,318,024 A | 6/1994 | Kittrell et al. | |
| 5,334,191 A | 8/1994 | Poppas et al. | |
| 5,339,347 A | 8/1994 | Slatkin et al. | |
| 5,413,106 A | 5/1995 | Fujita et al. | |
| 5,419,323 A | 5/1995 | Kittrell et al. | |
| 5,421,337 A | 6/1995 | Richards-Kortum et al. | |
| 5,501,680 A | 3/1996 | Kurtz et al. | |
| 5,507,790 A | 4/1996 | Weiss | |
| 5,531,740 A | 7/1996 | Black | |
| 5,628,744 A | 5/1997 | Coleman et al. | |
| 5,653,706 A | 8/1997 | Zavislan et al. | |
| 5,693,043 A | 12/1997 | Kittrell et al. | |
| 5,830,208 A | 11/1998 | Muller | |
| 5,830,211 A | 11/1998 | Santana et al. | |
| 5,836,872 A | 11/1998 | Kenet et al. | |
| 5,860,967 A | 1/1999 | Zavislan et al. | |
| 5,865,754 A | 2/1999 | Sevick-Muraca et al. | |
| 5,868,731 A | 2/1999 | Budnik et al. | |
| 5,873,875 A | 2/1999 | Altshuler | |
| 5,885,211 A | 3/1999 | Eppstein et al. | |
| 5,944,748 A | 8/1999 | Mager et al. | |
| 6,015,404 A | 1/2000 | Altshuler et al. | |
| 6,027,496 A | 2/2000 | Loomis et al. | |
| 6,045,511 A | 4/2000 | Ott et al. | |
| 6,059,820 A | 5/2000 | Baronov | |
| 6,063,108 A | 5/2000 | Salansky et al. | |
| 6,074,382 A | 6/2000 | Asah et al. | |
| 6,081,612 A | 6/2000 | Gutkowicz-Krusin et al. | |
| 6,165,170 A | 12/2000 | Wynne et al. | |
| 6,171,302 B1 | 1/2001 | Talpalriu et al. | |
| 6,190,377 B1 | 2/2001 | Kuzdrall | |
| 6,197,020 B1 | 3/2001 | O'Donnell, Jr. | |
| 6,208,886 B1 | 3/2001 | Alfano et al. | |
| 6,246,898 B1 | 6/2001 | Vesely et al. | |
| 6,273,884 B1 | 8/2001 | Altshuler et al. | |
| 6,315,772 B1 | 11/2001 | Marchitto et al. | |
| 6,352,502 B1 | 3/2002 | Chaiken et al. | |
| 6,383,177 B1 | 5/2002 | Balle-Petersen et al. | |
| 6,406,474 B1 | 6/2002 | Neuberger et al. | |
| 6,418,339 B1 * | 7/2002 | Essenpreis et al. | 600/476 |
| 6,436,127 B1 | 8/2002 | Anderson et al. | |
| 6,440,155 B1 | 8/2002 | Matsumae et al. | |
| 6,454,781 B1 | 9/2002 | Witt et al. | |
| 6,477,426 B1 | 11/2002 | Fenn et al. | |
| 6,483,595 B1 | 11/2002 | Yakovlev et al. | |
| 6,484,118 B1 | 11/2002 | Govari | |
| 6,508,813 B1 | 1/2003 | Altshuler | |
| 6,514,242 B1 | 2/2003 | Vasily et al. | |
| 6,514,278 B1 | 2/2003 | Hibst et al. | |
| 6,530,915 B1 | 3/2003 | Eppstein et al. | |
| 6,569,157 B1 | 5/2003 | Shain et al. | |
| 6,585,725 B1 | 7/2003 | Mukai | |
| 6,600,951 B1 | 7/2003 | Anderson | |
| 6,632,219 B1 | 10/2003 | Baranov et al. | |
| 6,652,512 B2 | 11/2003 | Ota | |
| 6,653,618 B2 | 11/2003 | Zenzie | |
| 6,676,654 B1 * | 1/2004 | Balle-Petersen et al. | 606/9 |
| 6,684,097 B1 | 1/2004 | Parel et al. | |
| 6,695,835 B2 | 2/2004 | Furuno et al. | |
| 6,736,833 B2 | 5/2004 | Coleman | |
| 6,758,845 B1 * | 7/2004 | Weckwerth et al. | 606/9 |
| 6,788,967 B2 | 9/2004 | Ben-Haim et al. | |
| 6,877,239 B2 | 4/2005 | Leitner et al. | |
| 6,939,344 B2 | 9/2005 | Kreindel | |
| 6,991,644 B2 | 1/2006 | Spooner et al. | |
| 6,997,923 B2 | 2/2006 | Anderson et al. | |
| 7,000,469 B2 | 2/2006 | Foxlin et al. | |
| 7,090,670 B2 | 8/2006 | Sink | |
| 7,101,365 B1 | 9/2006 | Sharon | |
| 7,135,033 B2 | 11/2006 | Altshuler et al. | |
| 7,204,832 B2 | 4/2007 | Altshuler et al. | |
| 2001/0007068 A1 | 7/2001 | Ota et al. | |
| 2002/0019625 A1 | 2/2002 | Azar | |
| 2002/0022829 A1 | 2/2002 | Nagase et al. | |
| 2002/0049432 A1 | 4/2002 | Mukai | |
| 2002/0161357 A1 | 10/2002 | Anderson et al. | |
| 2002/0173782 A1 | 11/2002 | Cense et al. | |
| 2003/0032950 A1 | 2/2003 | Altshuler et al. | |
| 2003/0034959 A1 | 2/2003 | Davis et al. | |
| 2003/0036751 A1 | 2/2003 | Anderson et al. | |
| 2003/0103212 A1 | 6/2003 | Westphal et al. | |
| 2003/0109787 A1 | 6/2003 | Black | |
| 2003/0167033 A1 | 9/2003 | Chen et al. | |
| 2003/0195592 A1 | 10/2003 | Black | |
| 2003/0216719 A1 | 11/2003 | Debenedictis et al. | |
| 2004/0019278 A1 | 1/2004 | Abend | |
| 2004/0045948 A1 | 3/2004 | Shalev et al. | |
| 2004/0098070 A1 | 5/2004 | Mohr et al. | |
| 2004/0100444 A1 | 5/2004 | Park et al. | |
| 2004/0133251 A1 | 7/2004 | Altshuler et al. | |
| 2004/0162596 A1 | 8/2004 | Altshuler et al. | |
| 2005/0010258 A1 | 1/2005 | Peterson et al. | |
| 2005/0045189 A1 | 3/2005 | Jay | |
| 2005/0049582 A1 | 3/2005 | DeBenedictis et al. | |
| 2005/0062720 A1 | 3/2005 | Rotzoll et al. | |
| 2005/0107852 A1 | 5/2005 | Levernier et al. | |
| 2005/0119552 A1 | 6/2005 | Hochman | |
| 2005/0135102 A1 | 6/2005 | Gardiner et al. | |
| 2005/0137584 A1 | 6/2005 | Lemchen | |
| 2005/0143719 A1 | 6/2005 | Sink | |
| 2005/0143793 A1 * | 6/2005 | Korman et al. | 607/94 |
| 2005/0154380 A1 | 7/2005 | DeBenedictis et al. | |
| 2005/0154381 A1 | 7/2005 | Altshuler et al. | |
| 2005/0154382 A1 * | 7/2005 | Altshuler et al. | 606/9 |
| 2005/0154431 A1 | 7/2005 | Quistgaard et al. | |
| 2005/0251118 A1 * | 11/2005 | Anderson et al. | 606/9 |
| 2005/0278002 A1 | 12/2005 | Eimerl et al. | |
| 2006/0004347 A1 * | 1/2006 | Altshuler et al. | 606/4 |
| 2006/0011024 A1 | 1/2006 | Azar et al. | |
| 2006/0122584 A1 | 6/2006 | Bommannan et al. | |
| 2006/0155266 A1 | 7/2006 | Manstein et al. | |
| 2006/0200115 A1 | 9/2006 | Ferren et al. | |
| 2006/0253176 A1 | 11/2006 | Caruso et al. | |
| 2007/0049996 A1 | 3/2007 | Black | |

FOREIGN PATENT DOCUMENTS

| | | | |
|---|---|---|---|
| WO | WO 99/11324 A1 | 3/1999 | |
| WO | WO 00/53261 A1 | 9/2000 | |
| WO | WO 01/23032 A2 | 4/2001 | |
| WO | WO 01/26573 A1 | 4/2001 | |
| WO | WO 03/017670 A1 | 2/2003 | |
| WO | WO 2004/037068 A2 | 5/2004 | |
| WO | WO 2004/083944 A2 | 9/2004 | |
| WO | WO 2004/086947 A2 | 10/2004 | |
| WO | WO 2005/016453 A1 | 2/2005 | |
| WO | WO 2005/018473 A1 | 3/2005 | |
| WO | WO 2005/027730 A2 | 3/2005 | |
| WO | WO 2007/027962 A2 | 3/2007 | |

OTHER PUBLICATIONS

PCT International Search Report and Written Opinion, PCT/US06/34132, May 15, 2007, 11 pages.

Anderson, D.E. et al., "System for the automated photothermal treatment of cutaneous vascular lesions," Journal of Biomedical Optics, Mar./Apr. 2004, pp. 308-314, vol. 9, No. 2.

Wyman, D.R. et al. "A Control Method for a Nonlinear Multivariable System: Application to Interstitial Laser Hyperthemia," IEEE Transactions on Biomedical Engineering, Sep. 1991, pp. 891-898, vol. 38, No. 9.

U.S. Appl. No. 60/458,770, filed Mar. 27, 2003, 36 pages.

U.S. Appl. No. 10/745,761, filed Dec. 23, 2003, 33 pages.

Welch, A.J., "Thermal Response of Laser Irradiated Tissue," IEEE Journal of Quantum Electronics, vol. QE-20, Dec. 1984, pp. 1471-1481, vol. 12.

U.S. Appl. No. 11/158,907, filed Jun. 20, 2005 (copy not enclosed).

U.S. Appl. No. 60/652,891, filed Feb. 14, 2005 (copy not enclosed).

U.S. Appl. No. 10/367,582, filed Feb. 14, 2003 (copy not enclosed).

U.S. Appl. No. 10/751,041, filed Dec. 31, 2003 (copy not enclosed).

U.S. Appl. No. 10/888,356, filed Jul. 9, 2004 (copy not enclosed).

U.S. Appl. No. 10/750,790, filed Dec. 31, 2003 (copy not enclosed).

U.S. Appl. No. 10/868,134, filed Jun. 14, 2004 (copy not enclosed).

Anderson et al, U.S. Appl. 60/258,855, filed Dec. 28, 2000, pp. 1-3, 5, 6, 8-15 and Figures 22A and 22B.

Hunte, Aisha, K., Examiner, USPTO, Office Action issued in related U.S. Appl. No. 11/737,696 dated as mailed Aug. 4, 2009.

* cited by examiner

METHOD AND APPARATUS FOR MONITORING AND CONTROLLING THERMALLY INDUCED TISSUE TREATMENT

CROSS-REFERENCE TO RELATED APPLICATIONS

This application claims priority under 35 U.S.C. §119(e) to U.S. Provisional Patent Application Ser. No. 60/712,358, "Method and Apparatus for Monitoring and Controlling Thermally Induced Tissue Treatment," by Leonard C. DeBenedictis, George Frangincas, Kin F. Chan, B. Wayne Stuart III, Robert Kehl Sink, Thomas R. Myers and Basil Hantash, filed Aug. 29, 2005. The subject matter of all of the foregoing is incorporated herein by reference in their entirety.

BACKGROUND OF THE INVENTION

1. Field of the Invention

The present invention relates to a method and apparatus for dermatological tissue treatment, and more particularly, to controlling dosage from an electromagnetic source based on measurements of a handpiece motion and/or skin tissue response.

2. Description of the Related Art

Many electromagnetic dermatological treatment systems require extensive training before physicians and nurses develop the skills to deliver energy uniformly over a treatment region, such as the face, neck, chest, or back. In many cases, physicians and nurses do not treat uniformly, resulting in uneven treatment, over treatment, or under treatment. There is a need to create more uniform photothermal and/or radio-frequency (RF) treatment, particularly for large areas.

Additionally, not all patients respond the same way to the same level of treatment. So even if precisely the same laser energy dose is delivered to two different patients, the response of each patient may be substantially different. Within a single patient, the skin response may vary from region to region. Treatment of the forehead may respond differently than treatment of the neck, for example. If uniform treatment parameters are used for all patients or for all regions, then the treatment parameters will typically be designed for the most sensitive patient or the most sensitive region in order to avoid undesirable side effects. Designing for the most sensitive region or patient will frequently lead to undertreatment of other regions or patients.

Many medical laser systems for the treatment of dermatological skin conditions function by pressing a footpedal to trigger the delivery of a single pulse of treatment energy. This type of treatment apparatus is slow and has a lot of repetitive motions, which can be tiring to the operator. Other laser treatment systems fire identical pulses at a constant pulse repetition rate as the user moves the handpiece across the tissue. This system requires skill and increases the risks of over- or under-treatment in the hands of an unskilled operator. Therefore, there is also a need for an approach to electromagnetic treatment that provides controlled dosage and adjusts the dosage level in real time to prevent over-and/or under-treatment.

Weckwerth U.S. Pat. No. 6,758,845 describes the use of optical measurements of regularly spaced indicia that are placed on or adjacent to the treatment region, but the concept is limited by the application of regularly spaced indicia that are counted to measure distance traveled by a handpiece. This requires the precise positioning of indicia to avoid errors. In addition, the visible indicia may be difficult to remove following treatment, and may leave an unsightly pattern on the skin following treatment.

Weckwerth '845 and Talpalriu U.S. Pat. No. 6,171,302 describe mechanical roller systems for tracking handpiece travel. These can be unreliable, for example, when used with gel due to a lack of friction between the mechanical roller and the skin surface. This leads to drop outs and errors in measurements of positional parameters. In addition, mechanical rollers can become rusted or gummed up so that they no longer spin easily, which makes dropouts and errors more likely. Wearing out of mechanical parts leads to similar errors.

Weckwerth '845 describes other systems that measure position of the handpiece indirectly, through the interaction with reference planes or points outside the target area, rather than measuring the target area directly. With this approach, the location of the treatment surface relative to the reference surface must be measured or controlled. In addition, these systems only measure one coordinate for the handpiece, which means that motion of the handpiece across the target tissue due to change in orientation of the handpiece may not be accounted for by the sensor systems. This leads to inaccuracies.

For treatment of large areas, an automatic laser control system is needed for adjusting laser treatment parameters in real time in response to the handpiece position, velocity, and/or acceleration or in response to the laser treatment itself. Thus, there is a need for an apparatus and method for a feedback loop that increases the effectiveness of treatment by controllably responding to treatment variables such as treatment speed, handpiece angle, handpiece acceleration, patient to patient variability, region to region variability within the same patient, etc. There is also a need for an apparatus and method that preferably enable faster and more reproducible treatments, that require less training and skill by the operator and/or that controllably respond to treatment variables. The apparatus and method preferably will also increase effectiveness without increasing side effects or invasiveness, treat with lower pain and side effects, directly measure treatment efficacy and/or progress for use in a feedback loop either alone or with other inputs instead of relying primarily on accurate delivery of a predetermined treatment dosage or on measurement of handpiece positional parameters, monitor biological response and treatment variables for improved biological predictability, efficacy, and safety, and/or permit better control of dosage, for example for photo-dynamic therapy (PDT) treatments, laser hair removal, or fractional laser resurfacing.

SUMMARY OF THE INVENTION

In general, the present invention comprises an apparatus and a method for treatment using feedback from one or more sensors that are used to measure handpiece positional parameters and/or the skin response to thermal or ablative treatment that is caused by the delivery of electromagnetic energy to the skin. The electromagnetic energy may be radio frequency (RF) or optical. The positional sensors and dosage evaluation sensors can be used separately or they can be advantageously combined to allow treatment to vary in response to a combination of skin response and handpiece positional parameters.

In one embodiment of the invention, a combination of relative and absolute handpiece positional measurements is measured to determine the positional changes of the handpiece relative to the treatment area.

In one embodiment of the invention, skin shrinkage is measured with a dosage evaluation sensor. In other embodiments of the invention, one or more measured responses of the skin include changes in one or more of the following: skin birefringence, skin water content, skin elasticity, skin mechanical damping parameters, skin color, skin features such as blood vessels and pigmented lesions, skin thickness, skin texture, and wrinkles. These and other skin changes may be measured usng one or more types of technology such as capacitive sensors, (hyper-) spectral imaging, terahertz imaging, optical coherence tomography, confocal microscopy, ultrasonic imaging, coherent detection, thermal detectors, thermal imaging systems, etc. Other skin responses and measurements can also be used.

In one embodiment of the invention, the output of an erbium doped fiber laser is collimated and deflected by a scanning delivery unit such as a galvanometer scanner or a starburst scanner as described in pending U.S. application Ser. No. 60/652,891 and in corresponding U.S. application Ser. No. 11/158,907, which are incorporated by reference herein, to create a series of figures at the treatment region.

In another aspect of the invention, the scanning rate of the scanning delivery unit is controlled by a controller to deliver a predefined pattern or dosage even if the handpiece velocity changes within a chosen range.

In one embodiment of the invention, a contrast enhancing agent is used to enhance the signal to noise ratio of the positional sensor. For example, FD&C Blue #1 can be applied to the surface of the skin to create an improved signal for a positional sensor comprising an optical mouse chip, CCD array, or other detector array, preferably with at least 25 elements. Using at least 25 elements as a 5×5 array is preferred because this allows sufficient image resolution to observe the changes in positional parameters and/or dosage response. If fewer detector elements are used, a more sophisticated algorithm and/or more sophisticated electronics generally will be typically required in order to distinguish changes in handpiece positional parameters and/or skin response. Other contrast enhancing agents are fluorescent or provide maximum contrast enhancement with IR or UV illumination. Wavelength selective coatings on the optical elements of the system may be used in conjunction with fluorescent contrast enhancing agents to filter out one or more illumination wavelengths. For example, the wavelength selective coatings can be designed to filter out light that is used to enhance the response of an optical positional sensor in order to improve the signal to noise ratio for a fluorescent emission signal at a different wavelength.

The contrast enhancing agent may be applied as a uniform or nonuniform pattern of similar or dissimilar shapes. This pattern of contrast enhancing agent can be applied using rollers, stamps, sprays, and/or stencils, for example. The contrast enhancing agent may also be applied onto or into an adhesive substance such as used in a temporary tattoo.

In selected embodiments of the invention, the positional sensor comprises one or more of the following: a mechanical mouse wheel or roller ball, non-concentric coils, an accelerometer, a gyroscope, transmitter(s) and receiver(s) that can be used to measure distance, a Doppler radar system, an ultrasonic time of flight measurement, etc.

In another embodiment of the invention, leading and trailing dosage evaluation sensors are used to measure the differential skin response due to thermal treatment.

In another embodiment of the invention, the scanning motion of a scanning delivery unit is not changed, but the pulse rate or pulse timing of the electromagnetic source is changed by the controller in response to measurements by at least one positional sensor and/or at least one dosage evaluation sensor. The pulse timing and scanner patterns may be chosen such that the beam is intentionally dragged across the treatment region to reduce the treatment intensity and/or to increase the size of each treatment zone created by each energy pulse.

In another embodiment of the invention, healthy skin is spared in regions between individual treatment zones to create fractional treatment. The spared tissue helps to promote rapid healing of the wounded area, prevent scarring, and allow higher treatment levels than are otherwise possible without side effects. The measurement of positional parameters can be used to accurately space the treatment zones from one another so that treatment dosage can be properly controlled.

In another embodiment, the density of fractional treatment is controlled through the use of feedback from positional and/or dosage sensors.

Other aspects of the invention include methods, devices, and systems corresponding to the approaches described above, as well as applications of the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 2C also depicts one possible treatment pattern created by this embodiment.

FIG. 10 illustrates an apparatus for measuring the shock wave signature with a piezo-electric material. FIG. 11 illustrates an apparatus for measuring the shock wave signature with a reflected probe beam.

DETAILED DESCRIPTION OF THE PREFERRED EMBODIMENTS

This invention describes an electromagnetic system with automatic adaptive control of (photothermal and/or RF) treatment parameters and/or activation. A nominal pattern and treatment rate may be defined when the system begins treatment and this treatment pattern can be modified based on algorithms that describe the skin response to treatment and/or the positional parameters of the handpiece. Which positional parameter measurements or skin response measurements are made may depend upon particular measurement results. For example, if the handpiece is moving very rapidly across the skin and treatment power is proportional to relative handpiece speed, then bulk heating of the tissue may be a concern. In this case, the dosage evaluation sensors may be instructed by the controller to measure skin parameters that are associated with blistering due to over treatment. If movement is slow, bulk heating and blistering may be less of a concern and more of the processing power of the controller can be used to make more accurate measurements of velocity with the positional parameter sensors instead. Detailed embodiments of the invention are described in the examples given below.

In some embodiments, a distinction can be made between micro-dosimetry and macro-dosimetry measurements. Micro-dosimetry measurements are substantially limited to one or more zones that are about to be treated by a pulse or a set of simultaneous pulses. For example, measurement of a 1.2 mm diameter area that is cocentered with a 1 mm diameter area that is about to be treated is micro-dosimetry because the measurement is substantially limited to the region that is about to be treated with a future pulse or a future set of essentially simultaneous pulses. In contrast, macro-dosimetry measurements are used to evaluate larger areas of skin to produce an average measurement of regions that include both areas that are about to be treated (or that have just been treated) and adjacent regions. In some embodiments, a dosage evaluation sensor is used to produce micro-dosimetry or macro-dosimetry measurements in accordance with the feedback loops of this invention.

Figure 1:
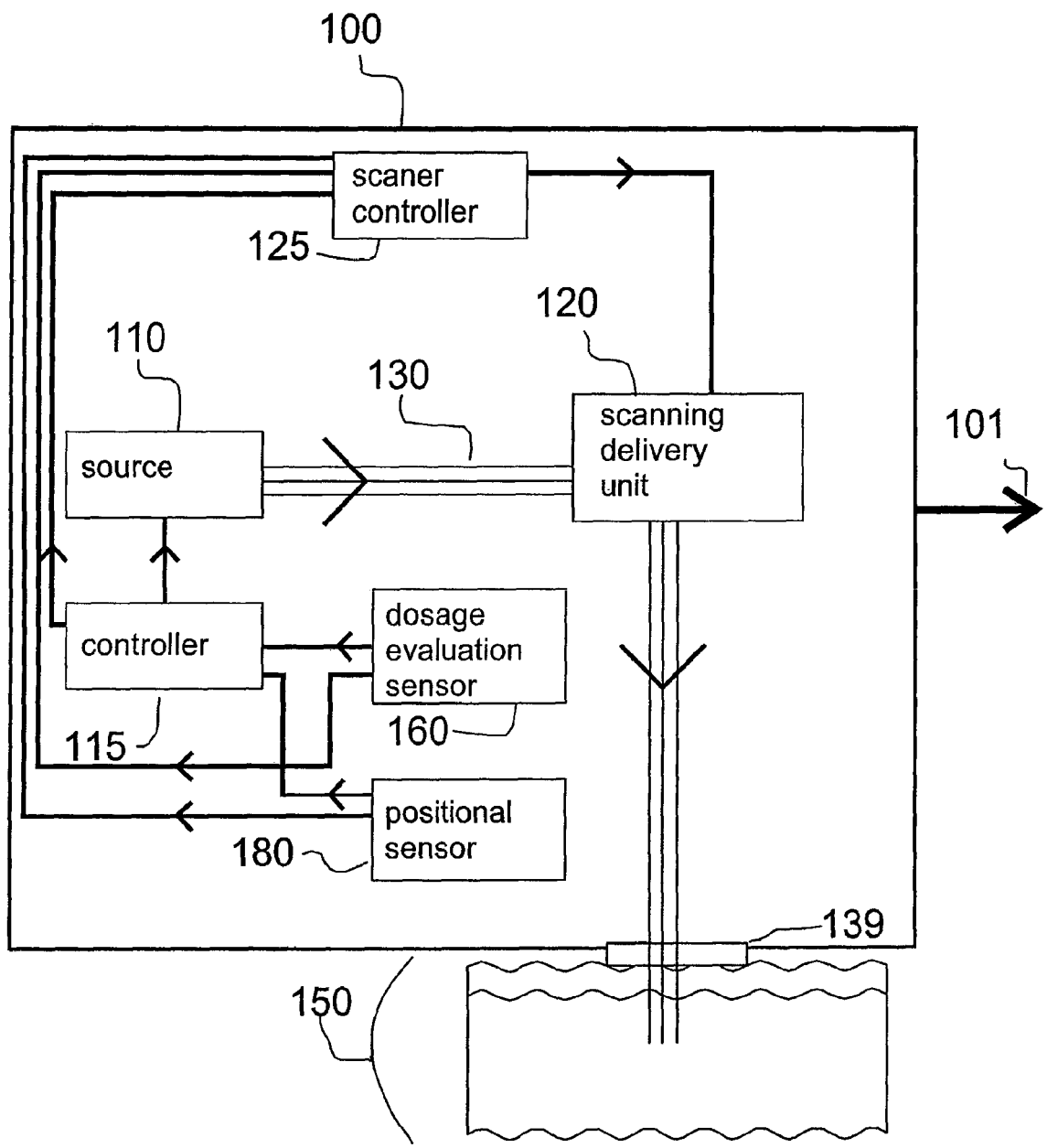
FIG. 1 is a diagram of an embodiment of the invention that incorporates a positional sensor and a dosage evaluation sensor.

FIG. 1 is a diagram of an embodiment of the invention showing a manually movable handpiece 100 that is configured to deliver electromagnetic treatment energy to the skin 150 in the treatment region. The electromagnetic source 110 generates electromagnetic energy 130 that treats the skin. The controller 115 activates or adjusts one or more parameters of the electromagnetic source for the purpose of affecting treatment. The handpiece 100 may contain a controller 115 that may comprise a computer, a radio frequency generator, and/or laser driver electronics. In other configurations, the controller 115 is located external to the handpiece 100 and is operably connected to the handpiece 100 to control treatment parameters. The system may also include an optional scanning delivery unit 120 that is operably coupled to a scanner control 125 that scans the electromagnetic energy 130 over the treatment region of the skin 150. An optional contact plate 139 that is mechanically coupled to the handpiece 100 may be used to make good electrical or optical contact with the skin 150 to enhance controlled delivery of the electromagnetic energy 130. A positional sensor 180 measures positional parameters of the handpiece and a dosage evaluation sensor 160 measures skin response to treatment.

While the operator manually moves the handpiece 100 in direction 101 or after the operator has manually moved the handpiece 100, the positional sensor 180 measures one or more positional parameters of the handpiece 100 and the dosage evaluation sensor 160 measures the skin response to treatment parameters. The positional sensor 180 and the dosage evaluation sensor 160 communicate with the controller 115 and/or with the scanner control 125. The controller 115 and/or the scanner control 125 materially alter the treatment in real time in response to the positional parameter measurements and/or in response to the dosage evaluation measurements.

In some embodiments, the feedback loops comprising the controller 115 and/or the scanner control 125 in combination with the positional sensor 180 and/or the dosage evaluation sensor 160 can be used to provide automated control of treatment parameters such as treatment location, treatment zone overlap, treatment energy, treatment depth, treatment power, treatment zone pattern, treatment cooling (including pre-cooling and post-cooling), etc. These treatment parameters can be controlled through adjustment of device parameters that affect treatment such as optical focus or spot size, pulse width, pulse energy, pulse timing, pulse frequency, laser power, laser wavelength, spray cooling volume, spray cooling timing, etc.

Figure 2A:
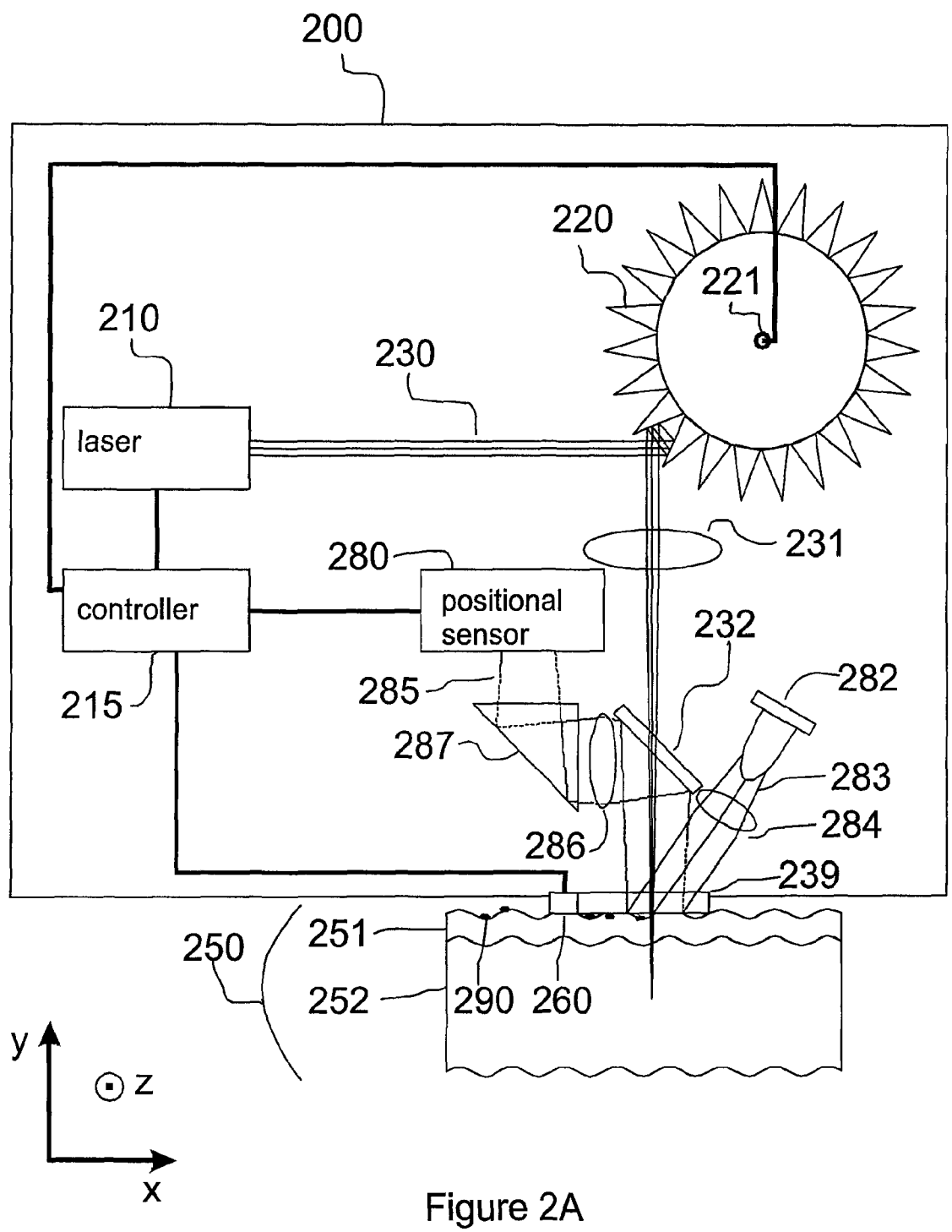
FIGS. 2A, 2B, and 2C are diagrams of an embodiment of the invention that incorporates an optical source, a starburst scanner wheel, and an optical positional sensor.

Optionally, the controller 115 may be operably connected to the scanner control 125, which can be helpful for reducing the number of wiring connections from the sensors. The controller 115 may serve the function of both the controller 115 and the scanner control 125 as shown in the embodiment of FIG. 2A. For example, the functions of both the controller 115 and the scanner control 125 can be performed by a computer or a CPU operably coupled to a memory that stores a computer program. The positional sensor 180 and the dosage evaluation sensor 160 may also be operably coupled or may be combined in a single component. For example, a CCD chip can be used to measure both shifts in movement and skin response.

Detailed embodiments of several components in FIG. 1 are described in the examples given below. In one embodiment, the electromagnetic source 110 delivers RF energy and the scanning delivery unit 120 comprises an electrical switching network comprising electrically controlled relays connected to multiple electrical contact pads in the contact plate 139 that is made of a nonconductive substance such as molded plastic. The scanning delivery system 120 can deliver patterns of energy across the treatment region sequentially or multiple relays can be activated to energize a plurality of treatment zones simultaneously.

In general, an electromagnetic source 110 is a radio frequency (RF) source, an optical source, or a combination of the two. A RF source generates electromagnetic energy with a frequency in the range of 0.1-20 MHz and preferably in the range of 0.5-8 MHz. An optical source generates light, which is defined for this application as electromagnetic energy with a wavelength in the range of 300 to 12,000 nm. Optical energy is preferred over radio frequency energy because it permits the energy to be directed more accurately and more easily to the desired locations on the skin. RF energy can also be desirable, particularly for applications where deeper penetration or targeting of particular buried layers of skin are desired. The choice of RF or optical energy may also be made to reduce interference with a chosen type of dosage evaluation sensor and/or position sensor.

In a preferred embodiment, the electromagnetic source 110 is a laser and the electromagnetic energy 130 is a laser beam. Examples of lasers are Nd:YAG lasers, diode lasers, erbium fiber lasers, $CO_2$ lasers, Er:YAG lasers, Er:glass lasers, flashlamp-pumped lasers, free electron lasers, thulium fiber lasers, Raman shifted fiber lasers, dye lasers, gas lasers, Argon lasers, and ytterbium fiber lasers.

The skin response can be measured by one or more dosage evaluation sensors 160 employing one or more types of technology such as capacitive sensors, (hyper-) spectral imaging, terahertz imaging, optical coherence tomography, confocal microscopy, ultrasonic imaging, coherent detection, thermal detectors, thermal imaging, etc. In addition, one or more dosage evaluation sensor(s) 160 may measure skin birefringence, skin water content, skin elasticity, skin mechanical damping parameters, skin color, skin features such as blood vessels and pigmented lesions, skin thickness, skin texture, wrinkles, etc. Other types of measurement technology and other dermatological features and tissue properties that can be measured will be apparent to those skilled in the art.

A mechanical mouse or roller wheel with an encoder can also be used as a positional sensor 180. It is preferable, however, to use a non-mechanical positional sensor, which does not rely primarily on moving parts to measure positional parameters. Non-mechanical positional sensors advantageously improve measurement reliability on slippery surfaces and reduce the chance of mechanical failure in comparison to mechanical positional sensors.

In one embodiment of a non-mechanical positional sensor 180 coil sensors are used as described by Ben-Haim et al in U.S. Pat. No. 6,788,967, which is herein incorporated by reference. Three sensor coils that are mechanically coupled to the handpiece 100 in the appropriate orientations can be used to measure positional information, for example up to three dimensions and/or up to three angular orientations for the handpiece when the sensor coils are placed in the magnetic field generated by at least two radiators. Other geometries and numbers of radiators and sensor coils are possible for measurement of one-dimensional to six-dimensional positional parameters of the handpiece. Other non-mechanical positional sensors such as optical positional sensors are described below and may be detachable from the handpiece.

Figure 12:
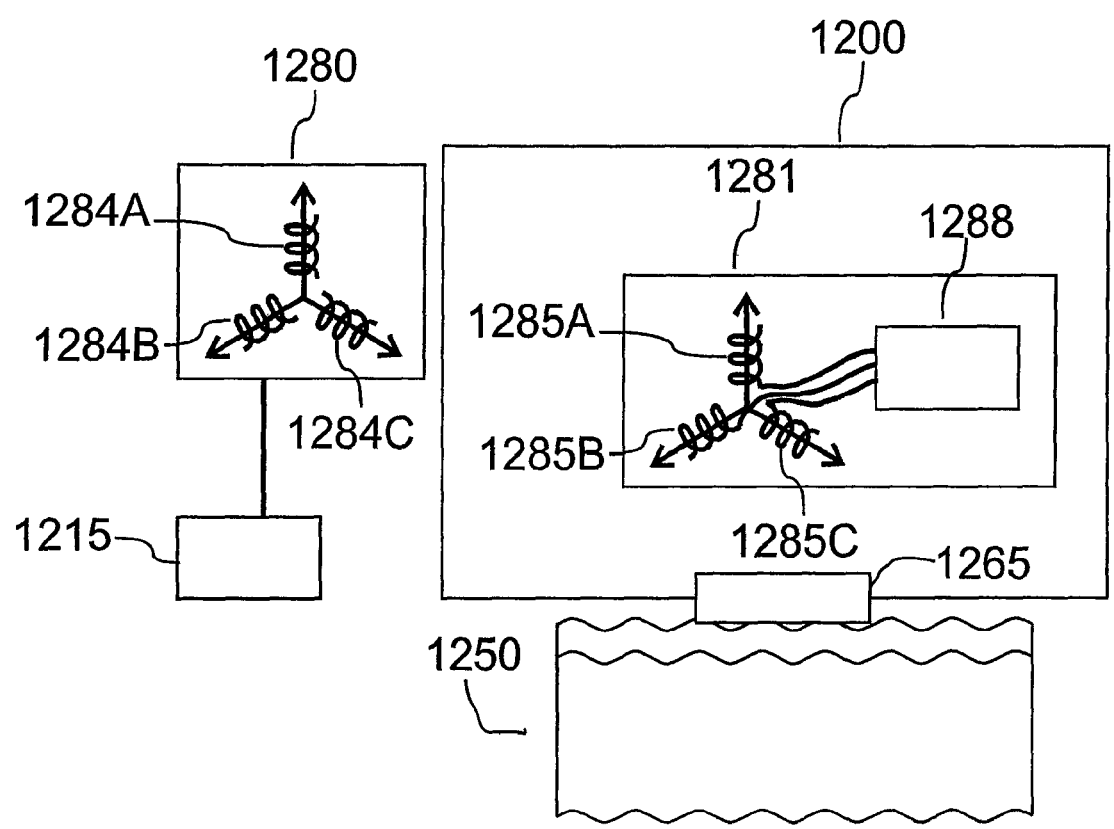
FIG. 12 is a diagram of an embodiment of the invention wherein one or more coil sensors are used to measure positional parameters of the handpiece.

One example of the use of coil sensors is shown in more detail in FIG. 12. In FIG. 12, a magnetic positional sensor 1280 is located outside the handpiece 1200 and the magnetic source 1281 is attached to the handpiece 1200. The magnetic source 1281 can comprise three magnetic field source elements 1285A-C. The magnetic field source elements are arranged such that their axes span three-dimensional space. The axes may, for example, directed in three mutually orthogonal directions. The magnetic positional sensor can comprise three magnetic sensor elements 1284A-C that can be located at a reference point and are arranged to span three-dimensional space.

In a preferred embodiment, each of the magnetic field source elements 1285A-C and each of the magnetic field sensor elements 1284A-C comprise a loop antenna that is tuned to a desired frequency, for example a frequency of about 10 kHz. The loop antennas 1285A-C for the magnetic field source elements 1282 can each be driven with a current source, for example an op-amp current source. Alternately, a single current source 1288 can be electronically switched to power each of the loop antennas of the magnetic field source elements 1285A-C sequentially. Preferentially, the system is operated in the near field of each of the magnetic field source elements 1285A-C and each of the magnetic field sensor elements 1284A-C, but operation in the far field is also possible. The source elements 1284A-C can be sequentially powered in order to time division multiplex the source signals. The controller 1215 comprises receiver electronics for measuring the response detected by the magnetic field sensors. The receiver electronics portion of the controller may be collocated with the magnetic field sensor elements 1284A-C or may be integrated with the other electronics of the controller 1215. The controller comprises appropriate electronics to demultiplex the received signals to identify the measured magnetic field intensity due to each of the source elements. To synchronize the systems, particularly in the case of time division multiplexing, a common clock can be used for the source and receiver electronics. Other configurations of source, receiver, multiplexing/demultiplexing, and electronic systems will be apparent. For example, additional embodiments and refinements of appropriate magnetic field systems can be found in U.S. Pat. Nos. 4,613,866, 4,737,794, 4,742,356, and 5,307,072, each of which is incorporated herein by reference.

In alternate embodiments, the magnetic field source elements 1285A-C are located at one or more reference points outside the handpiece and the magnetic field sensor elements 1284A-C are attached to the handpiece. The location of and direction of the treatment beam(s) emitted from the handpiece relative to the reference coordinate system is then measured. For treatment on the face, the handpiece 1200 can include the magnetic source 1281, and a small earbud that is placed within the ear of the patient can contain the magnetic positional sensor 1280. To improve accuracy and to determine whether the earbud has fallen out or shifted, a second magnetic positional sensor (not pictured) may be used, for example in the opposite ear of the patient. If there is a discrepancy between the redundant sensors, the system can alert the physician, using for example an audible alarm.

The choice of which of the magnetic source 1281 and the magnetic positional sensor 1280 is located at the reference point(s) and which is located at the handpiece 1200 can be chosen based on the sources of electromagnetic interference and objects of electromagnetic field distortion, such as metal plates. For the example above, it is anticipated that there is a scanning motor element, such as for example used in FIG. 2 to spin the scanner wheel 220 around axis 221, that generates a significant magnetic field. The effects of a scanning motor element on the measurement system can be reduced by locating the source in the handpiece instead of the sensor. In an alternate configuration, there may be no electromagnetic elements in the handpiece, for example, and the sensor would then be optimally located in the handpiece and the source located at a reference point. In addition, the system can be calibrated empirically to compensate at least partially for any fixed elements that distort the magnetic field.

Figure 13:
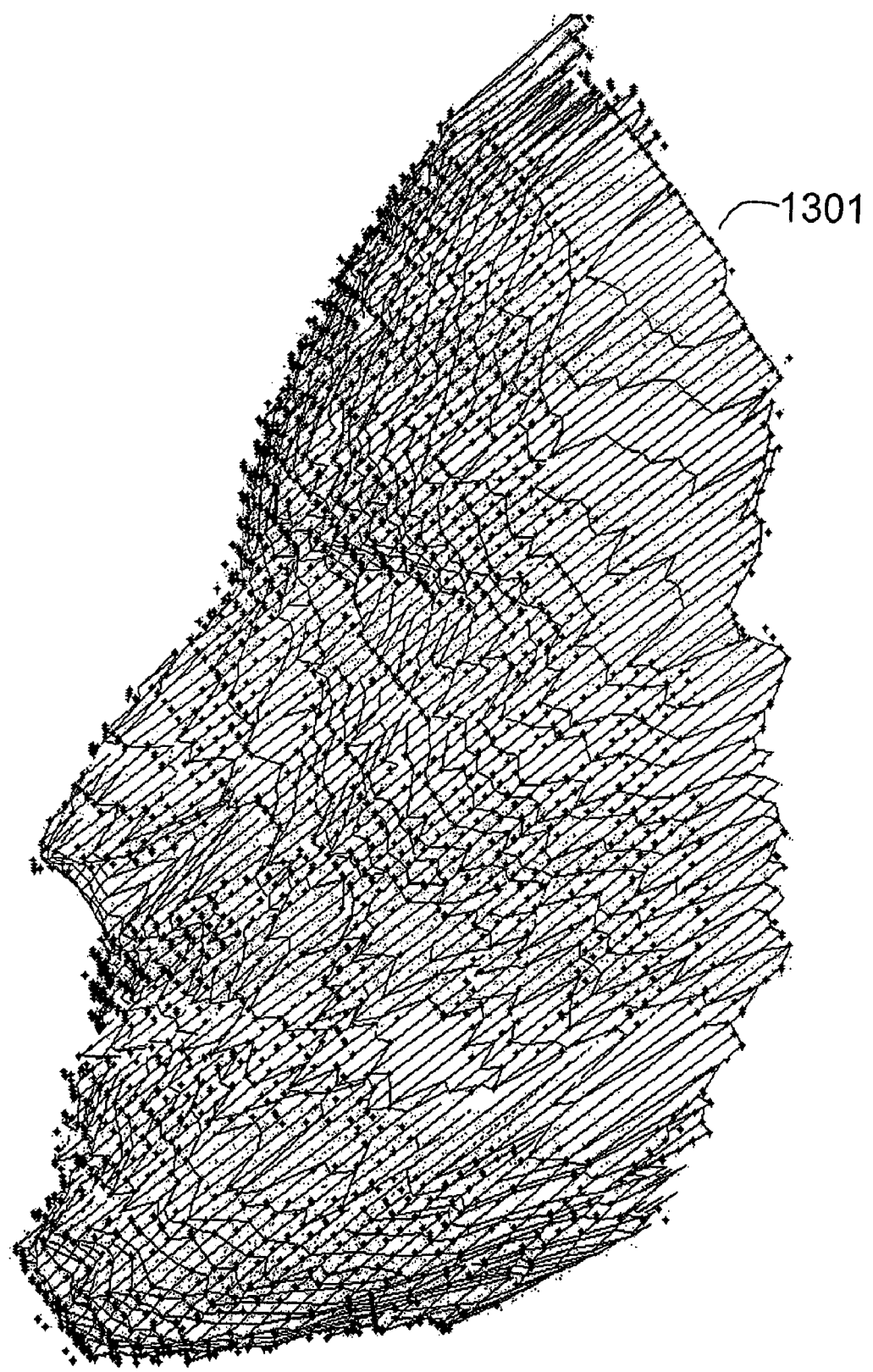
FIG. 13 illustrates measurements created by a system according to FIG. 12.

In one embodiment of a magnetic field system as described in FIG. 12, a Polhemus Patriot digital tracker system (available from Polhemus of Colchester, Vt.) is used to measure the position of the handpiece relative to a reference point. An example of measurements created using this system are shown in FIG. 13, which shows a 2D projection 1301 of a 3D data set for half of a face.

In one embodiment of the invention, one or more measured handpiece positional parameters include handpiece position or handpiece angle (angular orientation) or the time derivatives of these two parameters including handpiece velocity, handpiece acceleration, handpiece angular velocity, and handpiece angular acceleration. Handpiece positional parameters can be absolute or can be relative to the treatment region.

To enhance the serviceability of the apparatus and to allow handpieces to be interchanged and thus share expensive components, the handpiece may be detachable from one or more of the following: the electromagnetic source 110, the controller 115, and the scanner controller 125. To reduce the weight of the handpiece, these components may be located outside the handpiece. Alternatively, to enhance portability of the apparatus, these components may be included inside the handpiece.

The scanning delivery unit is configured to receive the electromagnetic energy 130 and deliver the electromagnetic energy 130 to the skin 150 regardless of where the other components are housed. For example, the electromagnetic source 110 may be a laser. The electromagnetic radiation may be coupled into an optical fiber, optical waveguide, or articulating arm for delivery to the handpiece. The handpiece can accept optical energy by using a fiber coupling or a fiber collimator. Similarly, it will be evident to those skilled in the art that the sensors 160 and 180 should be operably coupled to the controller 115, but do not need to be located inside the handpiece.

The controller 115 and scanner control 125 may be separate components as in FIG. 1 or may be combined as a single controller as shown in FIG. 2A.

In the embodiment of FIG. 2A, a laser source 210 is used as the electromagnetic source. In this embodiment, a manually movable handpiece 200 is configured to deliver an optical beam 230 of electromagnetic energy to the treatment region of the skin 250. The handpiece 200 contains a controller 215 comprising a computer and/or laser driver electronics. The controller 215 controls an optical source 210 and a scanning delivery unit 220 to affect one or more parameters such that treatment is materially affected. The optical source 210 generates an optical beam 230 that is directed to an optional scanning delivery unit 220. The scanning delivery unit 220 deflects the laser beam 230 to different treatment zones on or within the skin 250 as will be described in greater detail below. For clarity, only one beam position is shown in FIG. 2A. A dichroic mirror 232 and a contact plate 239 that are substantially transparent at the wavelength of the laser beam 230 may advantageously be included in particular embodiments. The deflected laser beam 230 is delivered through the dichroic mirror 232 and contact plate 239 to the skin 250. A beam delivery lens 231 can be used to focus the deflected beam 230 within the epidermis 251, dermis 252, or other layers of the skin 250. The focal point of the optical beam 230 may be below the skin surface or the beam may be diverging or collimated as it enters the skin 250. The dosage evaluation sensor 260 is mechanically coupled to the handpiece 200 and measures the skin response to treatment.

In the embodiment of FIG. 2, the positional sensor 280 measures the position of the handpiece relative to the surface of the skin 250. In alternate embodiments, the positional sensor 280 could measure position, velocity, and/or acceleration of handpiece relative to the surface of the skin 250. An illumination source 282 emits illumination 283 that is collimated by an illumination delivery lens 284 for delivery to the surface of the skin 250. Collimating the illumination 283 increases alignment tolerances, improves uniformity of the illumination on the skin surface, and allows the illumination source 282 to be placed further from the treatment region than would otherwise produce a uniform profile of illumination 283 at the surface of the skin 250. The illumination 283 is scattered from the surface of the skin 250 or from a contrast enhancing agent 290 that is placed in or onto the skin 250. The spectral reflectivity of the dichroic mirror 232 and the reflective prism 287 are designed to substantially reflect the wavelength of the scattered illumination 285. A detector lens 286 is placed in the optical path from the skin to the positional sensor 280 to image the surface of the skin 250 on the optical positional sensor 280. Examples of optical positional sensors 280 include an optical mouse chip (Agilent Technologies, Palo Alto, Calif.), a CCD camera, or an optical sensor array of at least two sensor elements. Preferably the optical sensor array has at least 25 sensor elements, arranged as a 5×5 array to have sufficient resolution to accurately quantify a range of velocity resolutions easily. Preferably, this optical positional sensor is silicon-based so that it can be manufactured cheaply using bulk manufacturing processes and cheap material sources that have been developed for the electronics industry. Other configurations will be evident to those skilled in the art.

Figure 2B:
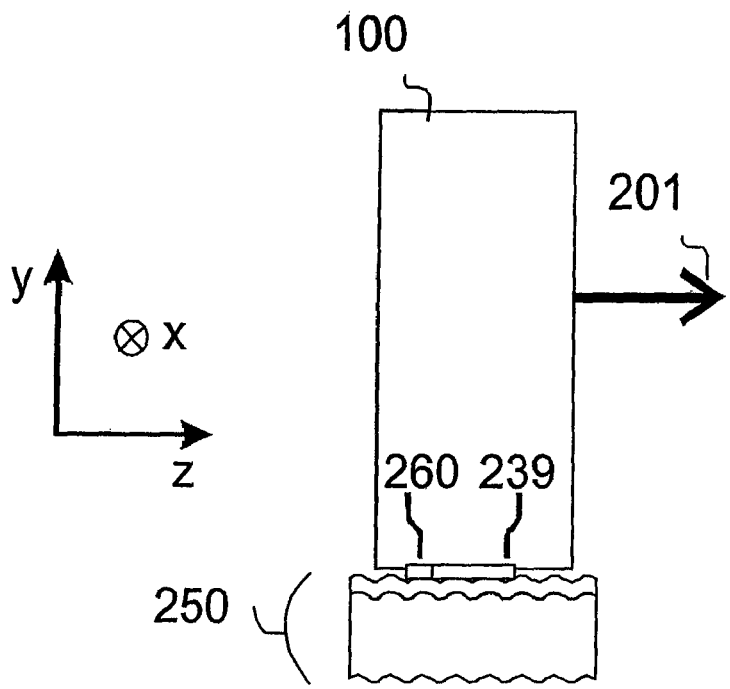

In FIG. 2A, the direction 201 of handpiece motion (not shown) is essentially perpendicular to the plane of the page. FIG. 2B illustrates a side view of the handpiece that shows the direction of motion 201 of the handpiece 200. For simplicity, internal elements of the handpiece 200 are not shown in FIG. 2B. The handpiece 200 is manually moved by the operator in direction 201 while the positional sensor 280 measures one or more positional parameters of the handpiece and the dosage evaluation sensor 260 measures one or more skin responses to treatment. The positional sensor 280 and the dosage evaluation sensor 260 communicate with the controller 215. In response to the measurements, the controller 215 adjusts the optical treatment parameters in real time to materially affect the photothermal treatment. For example, the rate of laser firing can be adjusted to be proportion to the velocity of the handpiece 200 to create a predefined treatment pattern or a uniform treatment.

Figure 2C:
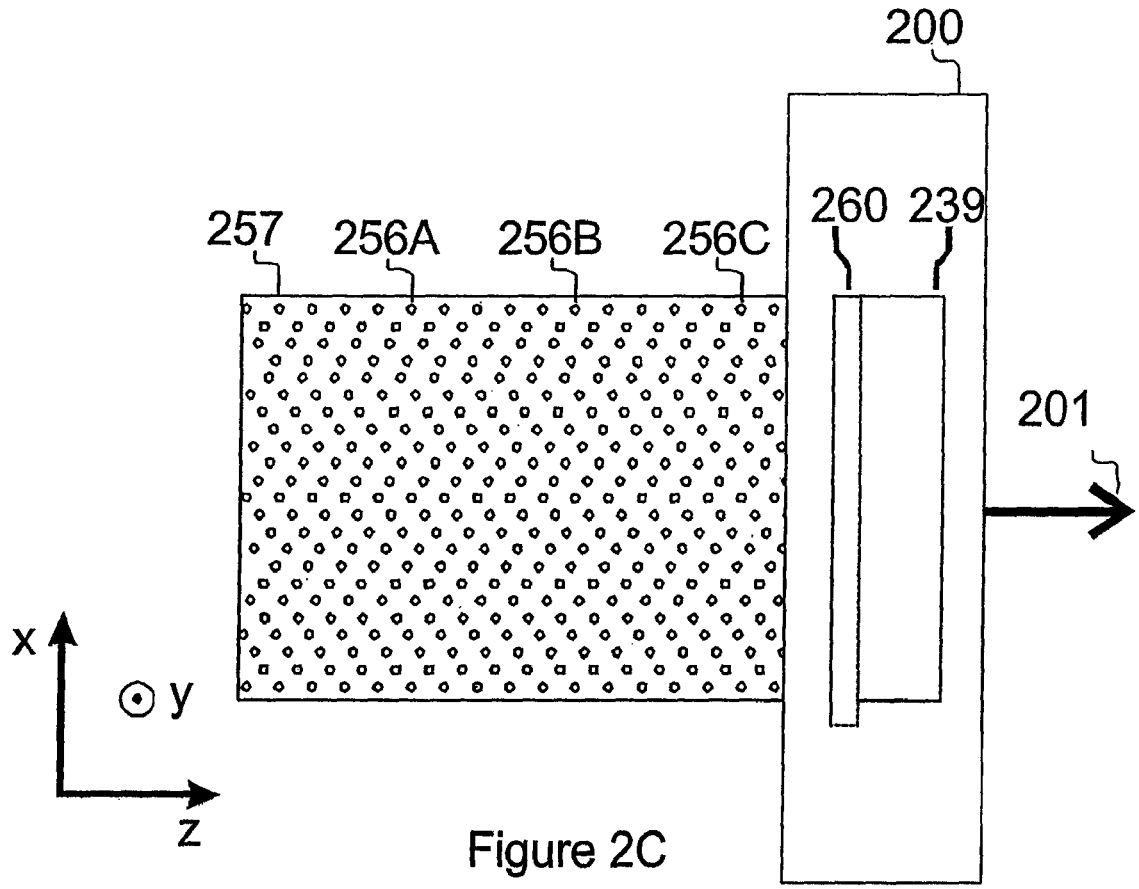

An example of a dosage evaluation sensor 260 is a capacitive sensor as shown in FIGS. 2A, 2B, and 2C. The capacitive sensor 260 can measure the level of desiccation of selected layers of the skin due to treatment. The measurements from the capacitve sensor 260 can be used to calculate the proper dosage parameters for the treatment and make adjustments to the treatment parameters using the controller 215. The capacitive sensor 260 can also be used to evaluate whether a region of skin has blistered. By imaging the junction between the dermis and the epidermis, the capacitive sensor can determine whether separation of the dermis and epidermis has occurred. In other embodiments, sensors for measuring or imaging skin resistivity can be used as dosage evaluation sensors 260 to evaluate blistering and skin moisture content. A capacitive sensor array that is commonly used for fingerprint measurements is an example of a sensor that could be used as a capacitive sensor 260.

FIG. 2C shows a treatment pattern comprising separated microscopic treatment zones 256 that can be created with this approach as the handpiece 200 is moved across the treatment region 257 in the direction 201. In this embodiment, separated microscopic treatment zones 256A, 256B, and 256C can be created in the skin as described in copending U.S. application Ser. Nos. 10/367,582, 10/751,041, 10/888,356, and 60/652,891, which are herein incorporated by reference. Preferably, the treatment zones 256 are created in a predefined pattern that is invariant with the relative velocity or acceleration of the handpiece 100. Other patterns will be evident to those skilled in the art. Substantially uniform treatment coverage can be created by appropriately choosing optics, treatment parameters, and laser pulse timing. Additionally, the capacitive sensor 260 may provide feedback to the controller 215 so that treatment parameters can be adjusted to reduce the density of microscopic treatment zones 256 or to reduce the treatment power in response to overtreatment.

In an alternative embodiment, the pattern can be intentionally varied according to a predefined algorithm where treatment rate is varied in real time in response to changes in the velocity or acceleration of the handpiece and where the treatment pattern is not predefined. For example, the treatment pattern can be controlled in real time by the user by appropriately adjusting the position, velocity, or acceleration of the handpiece. In some treatments, it is desirable to allow the operator to have control over the level of treatment through the use of velocity. For example, if the user treats quickly, the system may be configured to allow a higher level of treatment response as measured by the dosage evaluation sensor 260. If the user treats slowly, then the maximum allowable treatment response can be reduced. Thus, the user is able to control the treatment settings simply by changing positional parameters of the handpiece. Thus, the treatment pattern, treatment density, treatment intensity, and other treatment parameters may not be predefined, but may be defined through an automated response to measured positional parameters, to measured treatment response, or to both measured positional parameters and measured treatment response. An electronic or computer interface (not pictured) may be provided to allow switching on or off different modes of user control.

In another embodiment, a treatment status map is displayed on a monitor (not shown) for the user or the patient to observe. The positional sensor 280 can be used to measure the location within the treatment region of the tissue response that is measured by the dosage evaluation sensor 260. In this way, a map can display which parts of the treatment region have been treated and how each part of the treatment region has responded to treatment. The user can take the information on this map to make treatment uniform over the entire treatment region or to have treatment vary in a desirable manner such as treating area with deep wrinkles more heavily than less wrinkled areas. Alternatively, the system can be configured to automatically reduce or disable treatment in the regions that have already been adequately treated as the user continues to move the handpiece over the treatment region. A picture or schematic representation of the treatment region, such as line drawing of a face for treatment of wrinkles on the face, can be used as a background for a computer display of the map of the treatment response measurements.

The use of a postional sensor 280 and/or a dosage sensor 260 to create a map can be used beneficially, particularly with small beam sizes less than 1 mm in their smallest dimension. Using such a map, treatment can be turned on or off based on whether treatment has covered that area or not. The advantage of using a beam size of less than 1 mm is that the granularity of the beam size for treatments that are visually apparent after treatment will be less noticeable for such small beam sizes. Thus, the use of a positional sensor 280 and or a density sensor 260 is particularly suited to fractional treatment and/or treatments with a small beam size of less than 1 mm.

Controller 215, optical source 210, and other components may be external to the handpiece 200 instead of being included inside the handpiece as illustrated in FIG. 2A. The optical beam 230 can propagate to the handpiece through free space, through an articulated arm, or through a waveguide, such as an optical fiber. The handpiece 200 may be mechanically separable from or mechanically separate from the external components and the handpiece 200 may be configured to receive the optical beam 230 and/or the signal from the controller 215.

In a preferred embodiment, the electromagnetic source 210 is a single mode pulsed erbium doped fiber laser with a peak output power in the range of 5-50 W and a wavelength in the range of 1.52-1.62 μm. This laser source can be focused to an optical spot size in the range of 30-600 μm and preferably 60-300 μm on the surface of the skin. Pulse energies in the range 2-100 mJ and preferably in the range of 8-20 mJ can be used for these ranges of optical spot size, wavelength, and power. This preferred embodiment does not include surface skin cooling, but such cooling can be included if desired to reduce damage to the epidermis and dermal-epidermal junction.

The scanning delivery unit 220 used in this embodiment is a scanner wheel rotating at least 360° around an axis 221 as described in detail in U.S. application Ser. No. 60/652,891 and in corresponding U.S. application Ser. No. 11/158,907, which are incorporated by reference herein. Other scanner types will be apparent to those skilled in the art. For example, galvanometer scanners, pseudo stationary deflection (PSD) scanners as described in copending U.S. application Ser. No. 10/750,790, which is also incorporated by reference herein, polygonal scanners, light valves, LCD screens, MEMS based reflective scanners, and translation stages can be used for the scanning delivery unit for delivery of optical energy. Multiple scanning delivery units can be used in such systems to control multiple axes of deflection. For example, two galvanometer scanners can be used in series to scan the laser beam in two directions to cover an area on the surface of the skin 250. Alternatively, single scanning units can cause beam deflection in two directions as described in detail in U.S. application Ser. Nos. 60/652,891 and 11/158,907.

One algorithm that can be used to control operational parameters of the scanning delivery unit 220 is to adjust the rotational speed of a double or single wheel PSD scanner and the laser firing rate in proportion to the velocity of the handpiece. This allows microscopic treatment zones of fractional resurfacing to be placed in a predefined pattern on the skin.

Another algorithm for controlling treatment is to adjust the firing of the laser in approximate proportion to the relative velocity of the handpiece to create a predefined density of treatment zones. A uniform distribution of treatment zones across a treatment region by overlapping or abutting treatment zones can also be achieved. For example, if the scanner 220 shown in FIG. 2A is controlled to spin at a constant angular velocity as the handpiece 200 is moving across the surface of the skin 250, the laser firing can be pulsed to create the desired density of treatment zones within the treatment region by firing the laser only when it is aligned with a particular facet of the scanner that creates the desired distribution or density of treatment. Not every facet needs to be used. For a particular velocity, every facet may be used. If the velocity is reduced by a factor of three from this velocity, then only every third facet can be used to keep the same density. Preferably, the algorithm maintains a uniform distribution of treatment zones within the treatment region. Spinning the scanning wheel 220 at a constant angular velocity is preferable to requiring the angular velocity of the scanning wheel 220 to be proportional to the speed of the handpiece 200 because this configuration reduces the complexity of the motors, associated drive electronics, and encoders that are used to accurately control the angular velocity of the scanning wheel 220.

In another embodiment, the scanner wheel 220 is run at a velocity that drags the optical beam 230 across the treatment region. This wheel velocity may even be in the opposite direction of the direction that would compensate for movement of the handpiece. This intentional dragging of the optical beam 230 across the surface of the skin 250 can be created with either variable-velocity or fixed-velocity scanner systems. With the fixed-velocity system, for example, the pulse duration of the laser beam can be adjusted according to the velocity of the handpiece 200 such that the optical beam is dragged across the skin by approximately the same distance with each pulse. By changing the angular velocity of the scanner wheel 220 or by changing the pulse duration for the optical beam 230, the distance over which the optical treatment occurs for each pulse can be changed. The controlled dragging of the optical beam can, for example, be used to increase the fill factor for a fractional resurfacing treatment by making each microscopic treatment zone larger by increasing the distance over which optical treatment occurs. As the velocity of the handpiece 200 is reduced, the increased pulse duration prescribed by this algorithm may cause a reduction in treatment response as measured by the dosage evaluation sensor 260. Therefore, it may be desirable to increase the pulse energy to keep the tissue response the same.

The contact plate 239 beneficially reduces optical scattering from the skin surface for the treatment beam by creating a smooth surface that can be used to precisely and reproducibly position the skin relative to the focus depth of the optical beam 230. The contact plate 239 can also act as a thermal heat spreader or can conduct heat away from the surface to actively cool the skin when connected to a cooling source (not shown). The contact plate 239 and dichroic mirror 232 can comprise sapphire, fused silica, borosilicate glass, transparent plastic, or other transparent materials. The contact plate 239, dichroic mirror 232, and other optical components may have optical coatings applied on one or more sides to increase the efficiency of energy delivery into the skin or to enhance the reflectivity or transmission of the illumination 283 from the illumination source 282.

In some embodiments, the contact plate 239 may be undesirable and may be omitted. For example, in ablative laser treatments, it may be desirable to have the surface of the skin be mechanically free to enhance the ablation response of treatment.

To enhance the ability of the optical positional sensor 280 to read the positional parameters of the handpiece 200, a contrast enhancing agent 290 can be applied onto or into the skin 250. For example, uniform application of a dye to the surface of the skin 250 can preferentially decorate certain features, such as skin wrinkles or hair follicles, to create shapes that can be detected as objects by the positional sensor 280. The contrast enhancing agent 290 must be non-toxic when applied onto or into a patient's skin in amounts suitable for adequately enhancing measurements by the positional sensor 280. Preferably, the contrast enhancing agent and the materials and geometry chosen for the handpiece 200 and contact window 239 allow the handpiece 200 to slide easily over the surface of the skin 250.

Examples of contrast enhancing agents 290 are carbon particles, India ink, and FD&C Blue #1. Many other dyes, inks, particulates, etc. can be used as contrast enhancing agents when applied to the skin and when used with the appropriate positional sensor 280. The wavelength illumination source 282 can be chosen to maximize the signal to noise ratio of the measurement of the positional parameters of the handpiece 200. For example, a red LED with a peak wavelength in the range of 600 to 640 nm can be used with FD&C Blue #1.

In many cases, the contrast enhancing agent will be chosen such that it has a low absorption of the treatment energy or of the treatment wavelength in the case of optical treatment energy. In this way, the contrast enhancing agent will not interfere with the deposition of the treatment energy in the treatment region. In some cases, the contrast enhancing agent is chosen such that a measurable or observable parameter changes in response to the treatment energy. A change in the contrast enhancing agent can be used to determine where treatment has occurred, which allows the treatment to be touched up in areas where it is not even or uniform.

It is desirable to choose a contrast enhancing agent 290 that can be removed without abrasive or harsh scrubbing. Alternatively, a removal facilitation substance (not shown) can be applied prior to application of the contrast enhancing agent 290 to allow the dye to be removed more easily. Dimethicone, urea, and arginine are examples of removal facilitation substances. These substances may be applied prior to the contrast enhancing agent 290 to facilitate subsequent removal of the contrast enhancing agent 290. These substances can be applied using common solvents such as water, alcohol, or oil. Concentrations of the removal facilitation substance can be used, for example, in the range of 0.001M to 0.1M.

It is desirable to choose a contrast enhancing agent 290 that is not clearly visible when illuminated with typical room light and/or sunlight. Contrast enhancing agents 290 are said to be "hypovisible" if and only if the contrast enhancing agent is not readily visible on otherwise bare skin with the naked eye when illuminated with 400-650 nm light when the contrast enhancing agent 290 is applied such that the response of the detector 280 is beneficially and substantially enhanced when using an illumination wavelength from 300-400 nm or from 700-1100 nm. The use of hypovisible contrast enhancing agents 290 is desirable because the contrast enhancing agent 290 will be less visible after treatment even if not all of the contrast enhancing agent 290 is removed from the treatment region.

Many fluorescent inks, lakes, dyes, and particulates are examples of hypovisible contrast enhancing agents 290. Fluorescing agents are desirable because the wavelength of illumination can be filtered by the dichroic mirror 232 or by other optical components or coatings while the throughput of the fluorescent emission wavelength is maximized to improve the signal to noise ratio of the positional sensor 290. Polymer (PMMA) encapsulated fluorescent dyes are commercially manufactured by NewWest Technologies (Santa Rosa, Calif.). Other fluorescent materials include collagen, elastin, FD&C Orange No. 5, flavin adenine dinucleotide, flavin adenine mononucleotide, folic acid, niacin, nicotinamide, reduced nicotinamide adenine dinucleotide (NADH), porphyrins, pyranine (FD&C Green No. 7), pyridocine hydrochloride, quinine sulfate, riboflavin, riboflavin phosphate, tryptophan, uranine (fluorescein), or combinations thereof. The absorption and emission spectra for these substances are well published in the art. Other fluorescent materials that are well known in the art can also be used as the contrast enhancing agent 290, for example Carbazine, Coumarin, Stilbene 3, Kiton Red.

The intensity of fluorescent emission of pyranine varies with pH. So pyranine can be used to evaluate changes in barrier function and alert the user or automatically stop treatment or reduce treatment intensity if a break in the stratum corneum or a rupture of the skin occurs during treatment. Thus, the contrast enhancing agent 290 may also be used to improve the signal to noise ratio of the dosage evaluation sensor 260.

Indocyanine green (ICG) is an example of a contrast enhancing agent 290. Most contrast enhancing agents 165 can be diluted with water or other solvents to make them easier to apply or cheaper to use. The peak wavelength of ICG varies depending on the solvent and the concentration of ICG. For example, in water, ICG has an IR absorption peak at approximately 700 nm for high concentrations (e.g. 129-1290 µM) and at approximately 780 nm for low concentrations (e.g. 6.5-65 µM). For ICG in blood plasma, there is an absorption peak in the range of approximately 790-810 nm across a broad range of concentrations (6.5-1290 µM). In general, ICG typically has an absorption peak in the range of 650-850 nm for most solvents. ICG also has absorption peaks in the UV range. ICG does not have a strong absorption peak in the range of 400 to 650 nm, which makes it difficult to see with the naked eye. Thus, ICG is an example of a contrast enhancing agent that has low visibility to the human eye, but is easily discernable to a silicon based optical detector when illuminated appropriately. In non-fluorescing contrast enhancing agents, the wavelength (or wavelength range) of illumination can be chosen to be in a region where the peak absorption of the contrasting agent is at least 3 times, or preferably at least 10 times, stronger or weaker than that of skin. It is also desirable to have the peak absorption of the contrasting agent in the chosen wavelength (or wavelength range) to be at least 3 times, or preferably at least 10 times, stronger than the peak absorption within the wavelength range of 400-650 nm.

Figure 3A:
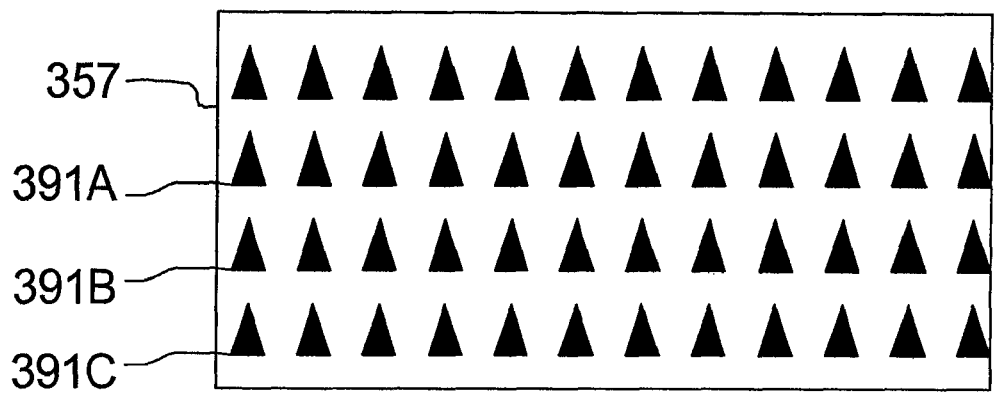
FIGS. 3A, 3B, and 3C are illustrations of patterns that can be applied to the treatment region or to regions adjacent to the treatment region to enhance the measurements of the optical positional sensor shown in FIG. 1.
Figure 3B:
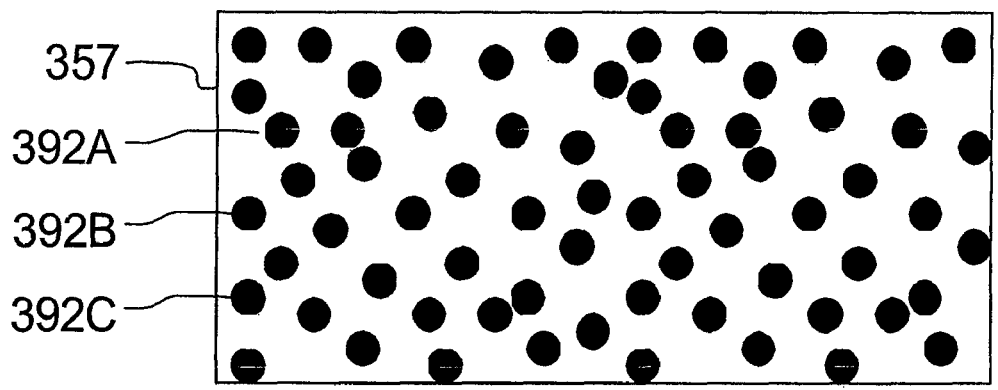
Figure 3C:
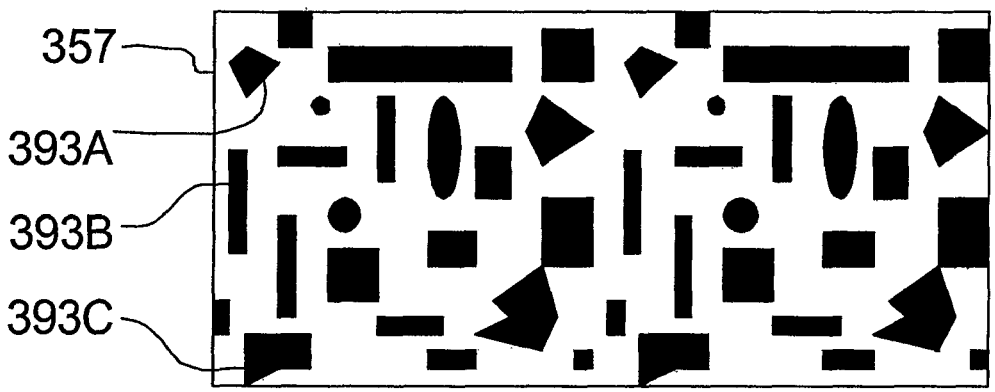

The contrast enhancing agent can also be applied in a pattern. The pattern may comprise a uniform grid of identical figures 391 in the treatment region 357 as illustrated in FIG. 3A. The pattern may comprise a nonuniform pattern of identical figures 392 in the treatment region 357 as illustrated in FIG. 3B. The pattern may comprise a nonuniform pattern of a plurality of different figures 393 in the treatment region 357 as illustrated in FIG. 3C. Contrast enhancing agents can be applied using stamps, rollers, sprays, stencils, or with agent-soaked gauze pads.

Patterns of contrast enhancing agents can also be attached to the skin using adhesives as used in temporary tattoos. As in a temporary tattoo, a pattern can be created by printing a contrast enhancing agent on or embedding a contrast enhancing agent in an adhesive that attaches to the skin. The adhesive has the advantage of being easier to remove than many of the contrast enhancing agents that can be included in or on the adhesive. Lakes of FDA approved colors such as FD&C Blue #1 (also packaged as Optiguide Blue by Reliant Technologies, Palo Alto, Calif.) can be embedded in a polymer-based tattoo adhesive and painted onto the skin. Following treatment, these adhesive based patterns can be removed with alcohol and light scrubbing. The use of adhesive also allows the use of contrast enhancing agents in doses that would otherwise be toxic to the skin because the adhesive can be designed to provide a barrier between the skin and the contrast enhancing agent.

Alternatively, contrast enhancing agents may be suspended in sugar-based or gel based solutions without patterning. These solutions can desirably be made viscous so that they do not drip outside the treatment area.

Instead of applying a pattern of figures with a contrast enhancing agent, the laser treatment zones may form a pattern of figures that is used to enhance the response of the positional sensor 280. For example, a $CO_2$ laser can ablate portions of the skin to create a pattern of ablated areas interspersed inside nonablated areas. This pattern can be illuminated with an LED to provide visible features that enhance the signal to noise ratio of an optical mouse chip functioning as a positional sensor 280.

Other embodiments of the positional sensor 280 are illustrated in FIGS. 4-7. Other embodiments of the dosage evaluation sensor 260 are illustrated in FIGS. 8-11. Using one or more of these sensors, different measurements can be made to optimize tissue treatment levels. Treatment densities and treatment levels can be kept constant or maintained within defined ranges by the controller 215 which appropriately adjusts treatment parameters of the electromagnetic source 210 and the scanning delivery unit 220.

The positional sensors and dosage evaluation sensors shown in FIGS. 4-11 can be added to or substituted into the embodiment shown in FIGS. 1 and 2. As will be apparent to one skilled in the art, many of these systems can be easily designed such that the region sensed by the dosage evaluation sensor is coincident with the region measured by the positional sensor and the region being treated. In situations where it is not desirable to have the two sensors coincident or where these two types of sensors interfere, the dosage evaluation sensor may be displaced along the x, y, or z directions relative to the positional sensor.

While the embodiment illustrated in FIG. 2 shows delivery of optical energy to the treatment region, monopolar or bipolar radio frequency (RF) energy can also be used in place of optical energy by replacing the contact plate 239 with a contact plate, contact electrodes, or needle electrodes that are configured to deliver RF energy to a desired treatment region under the control of a controller 215 that comprises a RF generator.

Figure 4:
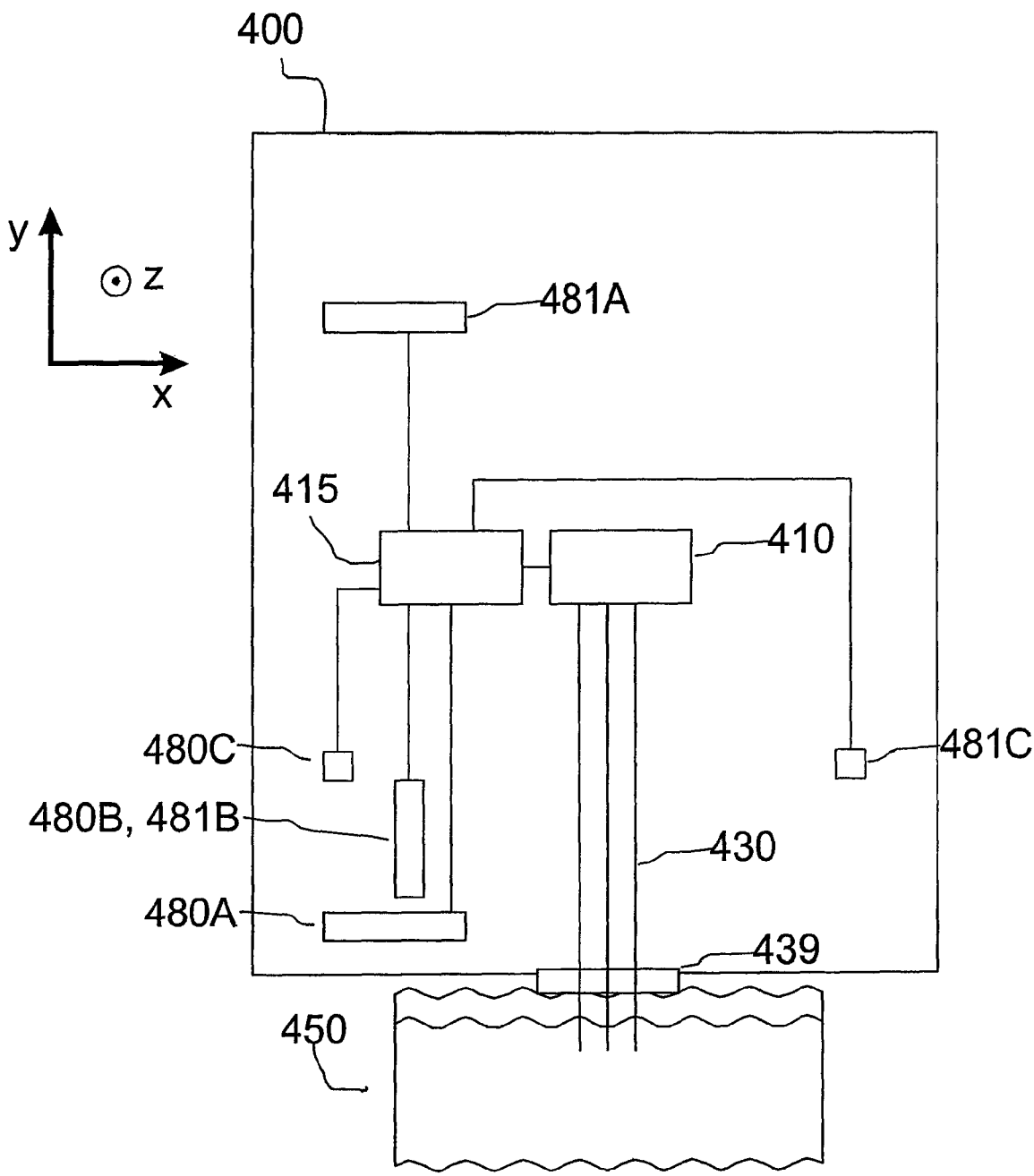
FIG. 4 is a diagram of an embodiment of the invention wherein one or more accelerometers are attached to the handpiece to measure positional parameters of the handpiece in up to three dimensions and/or up to three angular orientations.

FIG. 4 illustrates an embodiment of the invention. In this embodiment, the positional sensor is implemented as one or more sets of accelerometers 480 and 481 that are mechanically coupled to the handpiece 400. The sets of accelerometers 480 and 481 can be attached to the inside or outside of the handpiece 400. A set of three accelerometers 480A, 480B, and 480C can be used to measure changes in velocity in each of the three coordinate planes. The one or more sets of accelerometers 480 and 481 can communicate with a controller 415 that controls the operational parameters of an electromagnetic source 410. The electromagnetic source 410 emits electromagnetic energy 430, which is delivered to the skin 450 through a contact plate 439. The configuration illustrated in FIG. 4 can also include a scanning delivery unit (not shown), as illustrated in FIGS. 1 and 2.

As shown in FIG. 4, a pair of accelerometers can be used to measure angular acceleration in each of the three rotational directions. For example, accelerometers 480A and 481A measure the angular acceleration around a rotational axis parallel to the z axis, accelerometers 480B and 481B measure the angular acceleration around a rotational axis parallel to the x axis, and accelerometers 480C and 481C measure the angular acceleration around a rotational axis parallel to the y axis. Accelerometers 480B and 481B are displaced from each other along the z axis direction and are drawn as overlapping in FIG. 4. Alternatively, gyroscopes can be used to measure angular acceleration of the handpiece. MEMS based accelerometers and gyroscopes are sold by several suppliers (e.g. Kionix, Inc., Ithaca, N.Y.).

Measurements of acceleration or angular acceleration can be integrated in time to produce measurements of velocity and position or angular velocity and angular position. In many configurations, an initial calibration and periodic recalibrations may be required to reset the reference velocity, angular velocity, position, and/or angular position.

Accelerometers measure absolute positional parameters of the handpiece 400 rather than relative positional parameters of the handpiece 400 with respect to the treatment region of the skin 450. If relative positional parameters are desired, accelerometers can be used when the treatment region is immobilized or when absolute movement of the treatment region is insignificant. Alternatively, the absolute movement of the treatment region of the skin 450 and the absolute movement of the handpiece 400 can both be measured and the relative motion between the handpiece 400 and the treatment region of the skin 450 can be calculated.

Relative measurements of angular position can be used to provide feedback to the system and disable the laser unless the relative angle of the handpiece is within a certain angular range relative to the surface normal from the surface of the treatment region. This may be useful, for example, to align properly a cooling spray and a treatment laser beam on a treatment region. Absolute measurements of angular position are useful if the handpiece 400 has components that are sensitive to gravity, such as fluid-filled cavities that leak if turned upside down. Relative measurements of position can be used to measure distance between locations for pulsing the electromagnetic source 410.

Absolute or relative measurements of velocity, acceleration, angular velocity, and angular acceleration are useful for evaluating whether the handpiece has been dropped or has suddenly slipped in an uncontrolled way, which might lead to undesired treatment outside the desired treatment area. A combination of relative positional parameter measurements and absolute positional parameter measurements can be used to measure movement of the patient. For example, if the patient suddenly moves, the difference between the relative acceleration and the absolute accerlation measurements may be significant. In any of the situations described in this paragraph, the controller 415 may temporarily disable the electromagnetic source 410 to prevent treatment in areas that are not desired by the user.

Figure 5:
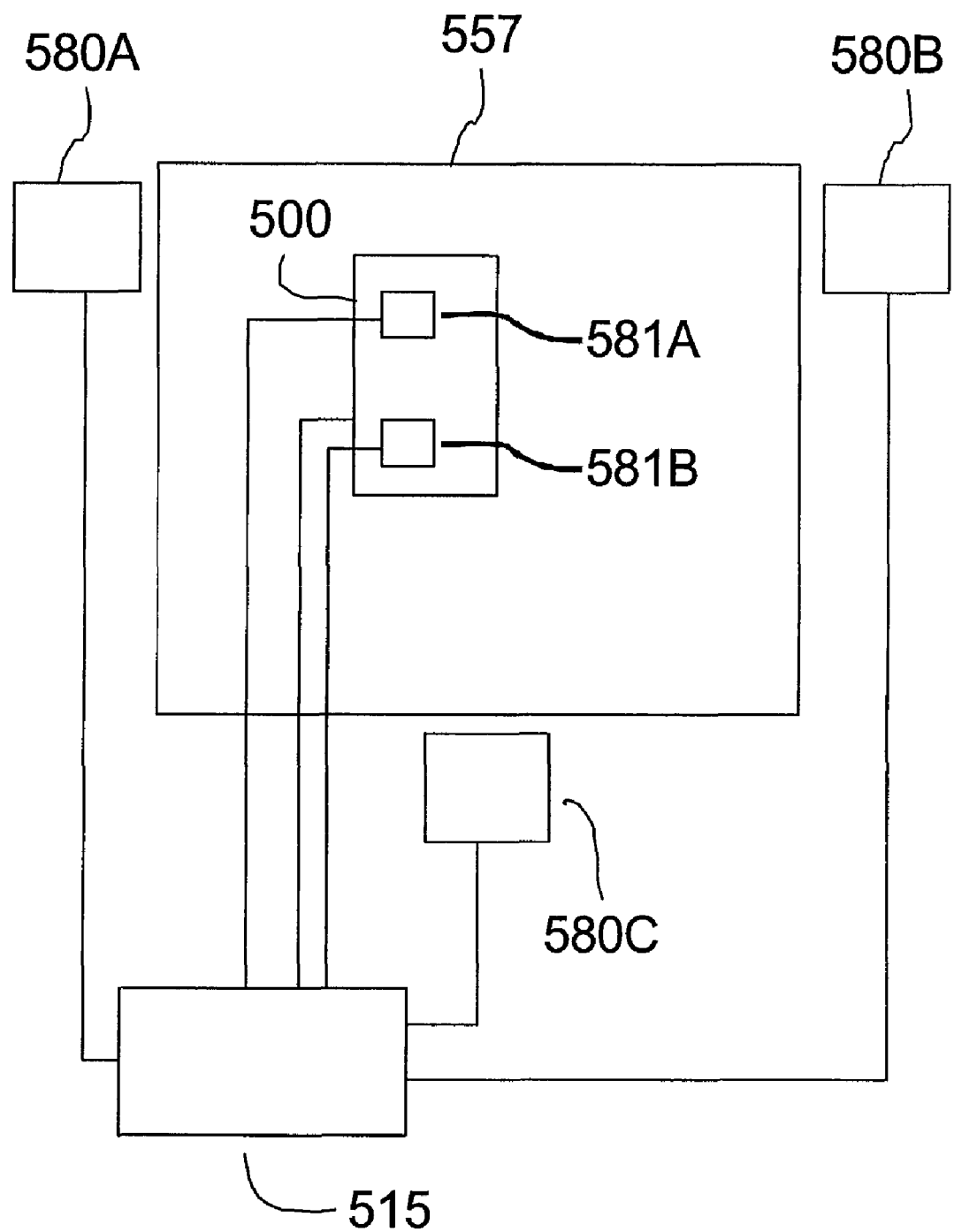
FIG. 5 is a diagram of an embodiment of the invention wherein transmitters and receivers are used to triangulate the position of the handpiece to measure positional parameters in up to three dimensions and/or up to three angular orientations.

FIG. 5 illustrates another embodiment of the invention. In this embodiment, the positional sensor comprises at least two pairings of transmitter and receiver that conduct either unidirectional or bidirectional wireless communication. The transmitters 580A-C are positioned to transmit signals to one or more receivers 581A-B that are mechanically coupled to the handpiece 500. The signals from the receivers are received by the controller 515, which uses time of flight measurements or phase measurements to calculate the distance between each pairing of transmitter and receiver. These distances can be used to calculate selected positional parameters of the handpiece, which can be done by the controller 515. The controller 515 may be operably connected to other components of the handpiece such as the electromagnetic source 110, the scanner control 125, or the scanning delivery unit 120 as shown in FIG. 1. These may be located inside or outside the handpiece 500 and, for simplicity, are not shown.

The number and location of transmitters and receivers determines the positional parameters that can be measured. For measuring the position of the handpiece in three dimensions, three transmitters and one receiver can be used. For measuring the position of the handpiece in up to three dimensions and also measuring the angular position for up to three independent angular directions, a second receiver can be used. For measuring all three dimensions and all three handpiece angles, three transmitters and three receivers are preferably used in order to have redundancy. A simple apparatus comprises two transmitters and one receiver. This apparatus can be used to measure the positional parameters of a handpiece in two dimensions along a predefined surface. In an alternate configuration, two receivers are used with one transmitter to produce the same measurement. The particular geometry and locations of transmitters and receivers can be generalized by one skilled in the art.

For simplicity in the examples described below, receivers are located on the handpiece and transmitters are located inside the treatment region 557 or are mechanically coupled to the treatment region 557 such that the measured positional parameters of the handpiece will be relative to the treatment region and not absolute measurements. Other configurations can be used if absolute measurements are desired. Light based or other electromagnetic communications systems can be used for these types of systems as well.

In one embodiment, three radio frequency transmitters are attached to a cap, preferably made of cloth or latex for ease of use and low cost. For example, transmitters can be attached to EEG caps for this purpose. This type of cap is useful for locating the handpiece when treating wrinkles on the forehead or periorbital areas of the face, for example, because the transmitters can be mechanically coupled to the treatment region. This type of cap can also be used with the coil measurement system described in the text for FIG. 1. In some embodiments, single chip receivers, similar to those commonly used in cell phones or GPS tracking systems, are attached to the cap. Alternatively, sensors or receivers can be attached directly to the treatment area or to other areas of the body, such as the teeth, ears, nose, chin, etc. using adhesives. If the sensors are placed accurately in the same place for each treatment, for example on the same tooth, then overlay maps can be created to illustrate the regions that were treated with each treatment in a series.

One advantage of the accelerometer, magnetic, gyroscope, and transmitter-receiver based measurement systems is that they can easily be used in noncontact mode, which reduces the chance of skin movement during treatment and allows the handpiece to be held at different distances from the skin in order to manually adjust the beam size that is incident on the skin surface.

Multiple positional sensors can also be used, for example, to allow lower quality signals from each of the positional sensors. For example, an optical mouse type sensor can be used with a magnetic radiator coil measurement system. The combination of multiple sensors can also be used to shut the system down if large discrepancies were noted between or among the sensors. If different types of sensors were used, discrepancies can be used to provide additional information, for example, about whether the skin is being stretched. This information can be used to detect situations when the handpiece is not sliding properly and can be used to provide feedback to the system and reduce localized over- and under-treatments.

Figure 6:
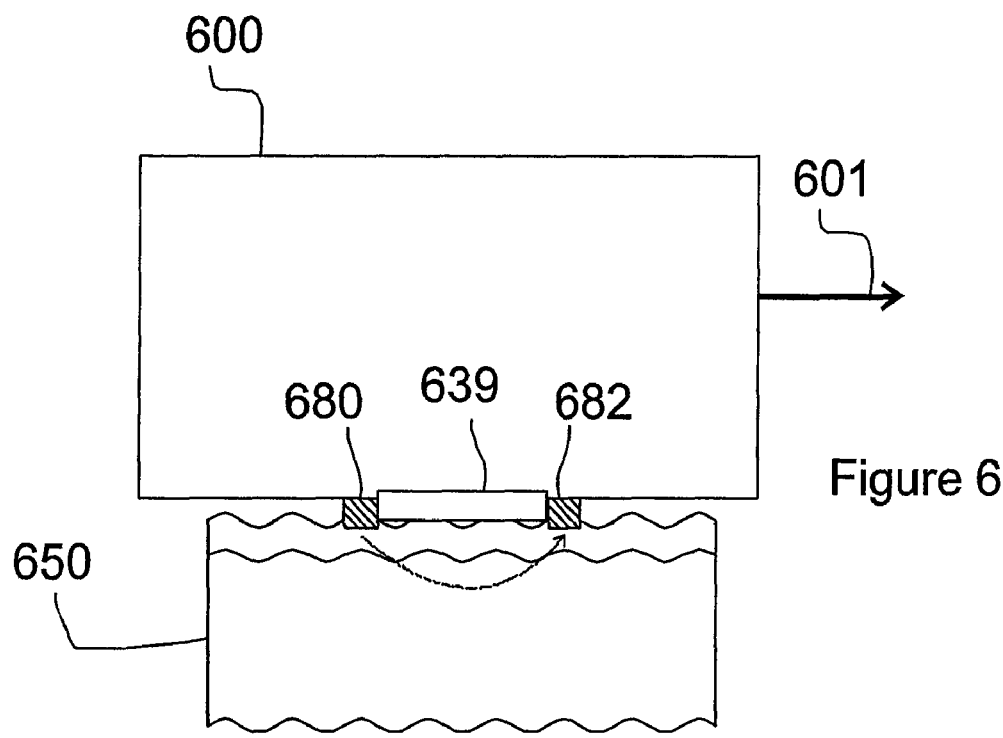
FIGS. 6 and 7 are diagrams of embodiments of the invention wherein at least one ultrasonic transmitter and at least one ultrasonic receiver are mechanically coupled to the handpiece. The embodiment depicted in FIG. 6 utilizes an ultrasonic time-of-flight measurement. The embodiment in FIG. 7 utilizes an ultrasonic reflection measurement.

FIG. 6 shows another embodiment of the invention wherein a manually movable handpiece 600 is configured to deliver optical energy to the skin. An ultrasonic transmitter 680 is positioned on one side of the contact plate 639 and an ultrasonic receiver 682 is positioned on the opposite side of the contact window. Time-of-flight measurements or phase measurements are recorded to measure the distance of propagation between the transmitter 680 and receiver 682. This can be used to measure velocity of the handpiece 600 in the direction 601 relative to the skin 650.

Figure 7:
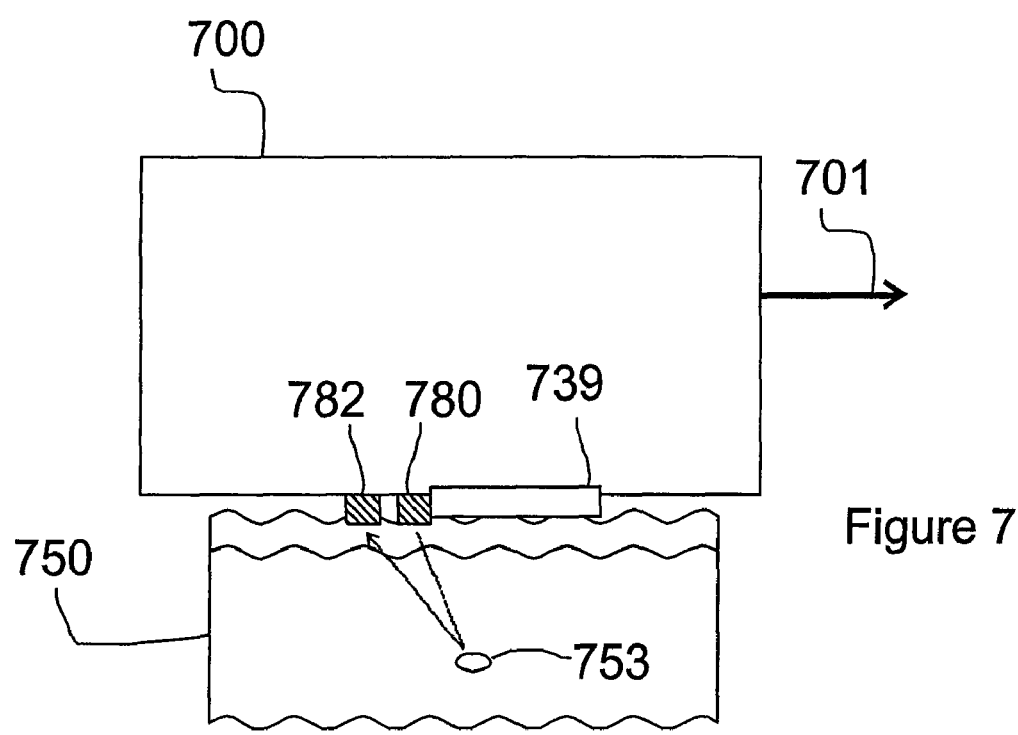

FIG. 7 shows an embodiment of the positional sensor and a handpiece 700. A phased array of ultrasonic transmitters 780 is positioned on one side of the contact plate 739 and an ultrasonic receiver 782 is positioned on the same side of the contact window. The phased array 780 emits a directional ultrasonic beam that can be scattered or reflected from the surface of the skin or from one or more features 753 within the skin to the ultrasonic receiver 782. Using phase shift, time of flight, or Doppler frequency shift measurements, a controller (not shown) can be used to measure positional parameters of the handpiece 700 as it moves in the direction 701.

The ultrasonic transmitter-receiver pairs shown in FIGS. 6 and 7 can also be used as embodiments of the dosage evaluation sensor 160 from FIG. 1 with the proper choice of frequency and preferably used in conjunction with a velocity sensor to remove the changes in the measurement due to velocity.

Figure 8:
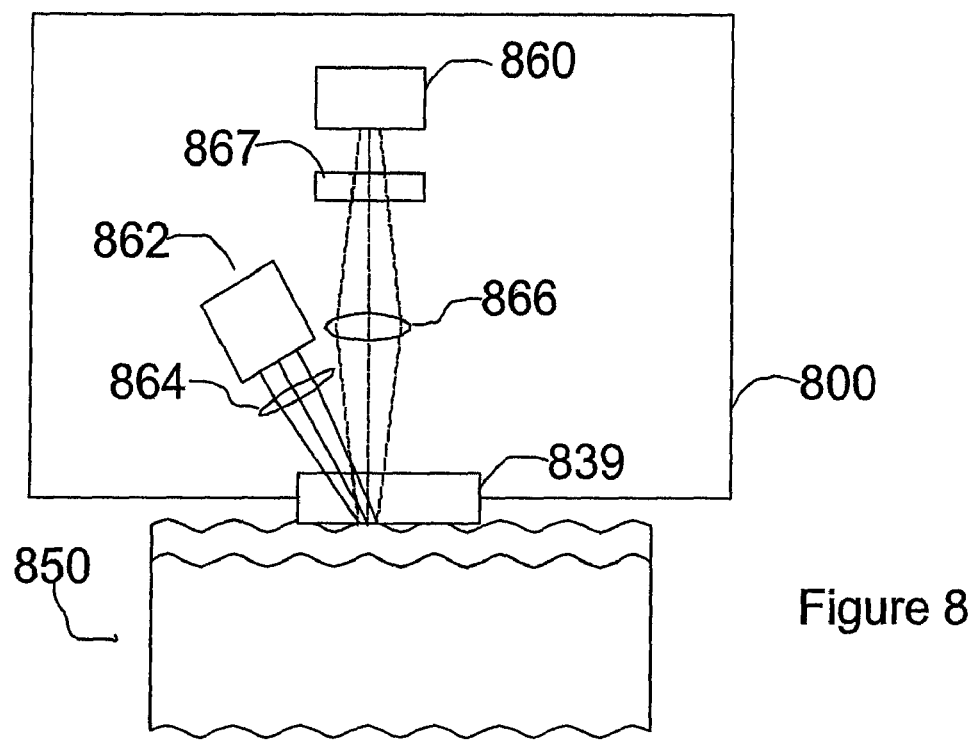
FIG. 8 illustrates an embodiment of the invention wherein polarized imaging is used to measure changes in the birefringence of the skin.

FIG. 8 shows an embodiment of the dosage evaluation sensor 160 from FIG. 1. In this embodiment, a polarized illumination source 862 is used to illuminate the skin 850 through an illumination lens 864 and through an optional transparent contact plate 839. A polarized imaging system comprising an imaging sensor 860, a polarizer 867, and an imaging lens 866 are used to image the birefringence of the treatment region of the skin 850. The imaging sensor 860 can then be operably coupled to the controller 115 shown in FIG. 1.

During certain types of photothermal treatment, dermal collagen is coagulated, which causes a loss of optical birefringence for the collagen. This change in birefringence can be measured by the imaging sensor 850 and can be used, for example, as the endpoint of a treatment pulse to control the duration of a treatment pulse.

The polarizer 867 may be adjustable (automatically or manually) to make alignment easier or more precise or to allow comparison of cross polarization and parallel polarization images.

The embodiment shown in FIG. 8 may also be used to measure skin shrinkage, preferably by measuring the separation distance between two features on the skin before and after treatment. One or more imaging sensors 860 can be used. Shrinkage can also be measured using a single measurement by measuring the separation distance between individual treatment zones that start at a known distance. For example, an ablative $CO_2$ laser can place two marks at a set distance of 15 mm and then the separation between these marks can be measured to determine skin shrinkage. The polarizer 867 may not be needed for these measurements and the illumination source 862 may be unpolarized.

In another implementation of the dosage evaluation sensor illustrated in FIG. 8, illumination can be used to increase the signal level of an optical dosage evaluation sensor. White light illumination can be used. Alternatively, sequential illumination with different color illumination sources can be used to capture images that are digitally processed to spectrally determine the treatment level of the tissue components. For example, illumination from a red LED at 660 nm and green LED at 555 nm can be used to capture, for which the absorption of melanin and blood are different. This will help to distinguish between treatment lightening response of pigmented lesions and of blood vessels. The polarizer 867 may not be needed for these measurements and the illumination source 862 may be unpolarized.

Figure 9:
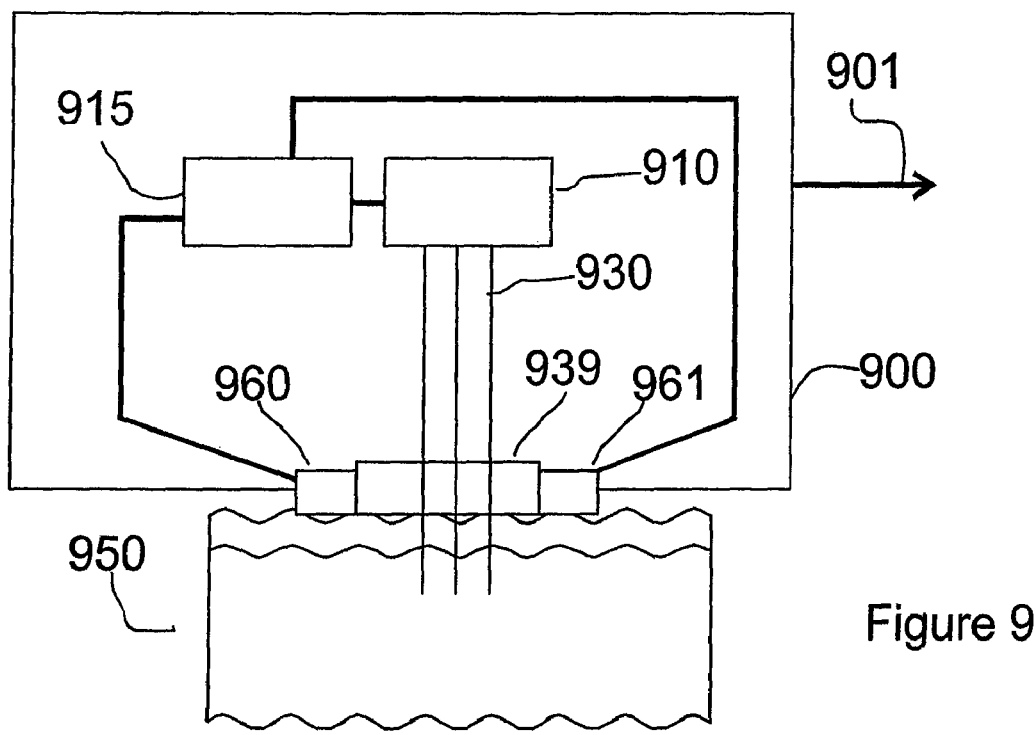
FIG. 9 is a diagram showing the use of leading and trailing dosage evaluation sensors in accordance with the invention for the measurement of the differential skin response to particular treatment parameters.

FIG. 9 shows an embodiment of the invention that uses a plurality of dosage evaluation sensors 960 and 961 to provide more information than is available from a single sensor. For example, one dosage evaluation sensor 961 can measure the dosage prior to treatment and a second dosage evaluation sensor 960 can measure the treatment response after treatment. In this embodiment, the two dosage evaluation sensors 960 and 961 are operably coupled to a controller 915 that controls the treatment parameters of the electromagnetic source 910. The electromagnetic source 910 generates electromagnetic energy 930 that is delivered to the treatment regions of the skin 950 through a contact plate 939 as the handpiece is moved in a direction 901.

Using a dosage evaluation sensor 961 before treatment and another dosage evaluation sensor 960 after treatment allows the controller 915 to calculate how much treatment is applied for a particular treatment setting. The controller 915 can then make adjustments as appropriate to adjust the parameters of the electromagnetic source 910. This dosage feedback loop allows real time adjustment of treatment parameters.

An example of a dosage feedback loop uses a first capacitive dosage evaluation sensor 961 and a second capacitive dosage evaluation sensor 960. Each capacitive dosage evaluation sensor measures the percentage of skin that has been treated with a nonablative fractional resurfacing treatment. The first and second capacitive dosage evaluation sensors 961, 960 are positioned in front of and behind the treatment window such that the first capacitive dosage evaluation sensor 961 measures the percentage of skin that had been treated prior to the current pass of the handpiece and the second capacitive dosage evaluation sensor 960 measures the percentage of skin that has been treated after the current pass of the handpiece over the treatment region. The difference between the measurements for the two sensors 960, 961 describes the percentage of skin treated during the current pass of the handpiece over the treatement region. The calculation of the percentage of skin treated during the current pass can be used, for example, to avoid overtreatment caused by bulk heating of tissue by reducing the laser treatment energy when unusually high percentages are calculated. Other examples of appropriate dosage feedback sensors 960, 961 are described in U.S. application Ser. No. 10/868,134, which is incorporated by reference herein.

Figure 10:
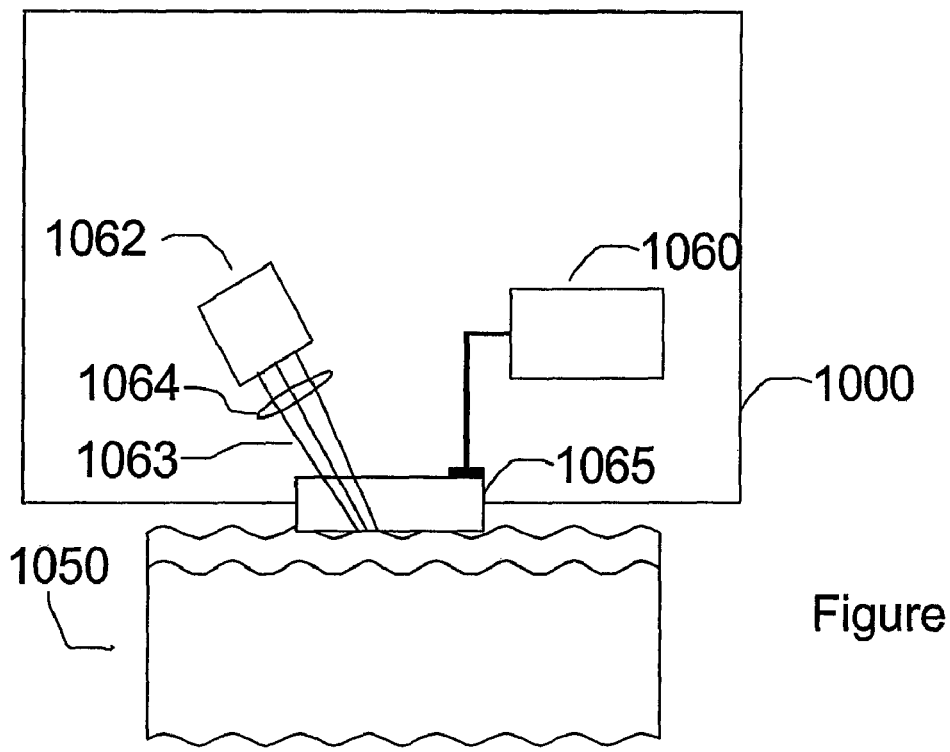
FIGS. 10 and 11 illustrate embodiments of the invention that measure the skin response to particular treatment parameters by measuring the signature of a shock wave created by an energy pulse incident on the skin.
Figure 11:
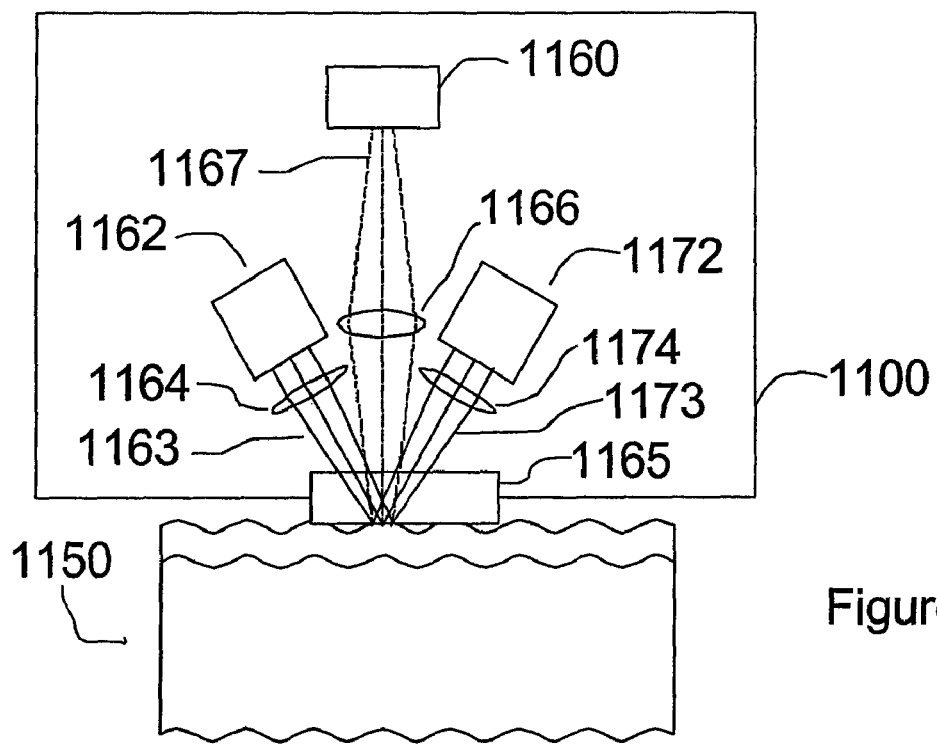

FIGS. 10 and 11 show other embodiments of a dosage evaluation sensor 1060/1160 that is operably connected to a controller (not shown), which changes the treatment parameters in response to the measurements from the dosage evaluation sensor. In a preferred embodiment, the dosage evaluation sensor 1060/1160 is located inside the handpiece 1000/1100. In alternate embodiments, the dosage evaluation sensor 1060/1160 is not located inside the handpiece 1000/1100. In FIG. 10, a probe radiation source 1062 generates a probe beam 1063, preferably with a pulse width of between 0.5 and 1000 ns or between 5 and 100 ns, that is absorbed by the skin 1050 to create a stress wave that propagates through the interface between a piezo-electric material 1065 and the skin 1050. The probe beam 1063 may pass through an optional probe beam delivery lens 1064 to focus the probe beam 1063 onto or into the skin 1050. The stress wave causes the piezo-electric material 1065 to generate an electrical signal that is measured by the electrical signal detector 1060 that is electrically connected to the piezo-electric material 1065.

The characteristics of the generated stress wave vary based on mechanical and optical characteristics of the skin. The probe wavelength can be chosen such that there is a difference in absorption within the skin between untreated and treated skin. Alternatively, the pulse conditions are chosen such that the mechanical response is different for treated and untreated skin. Thus, the stress wave that is created can be measured to determine whether the probed skin is approaching, has reached, or has exceeded a desired level of treatment. Examples of mechanical characteristics of the skin that can be probed using a stress wave include elasticity, tension, and mechanical damping of the skin.

The signature of the stress wave that is generated can be measured using several different techniques. One technique is illustrated in FIG. 10 and is described above. In this technique, a transparent contact plate 1065 made of a piezo-electric material, such as lithium niobate, generates an electrical signal in response to a mechanical stress wave. This electrical signal can be measured by an electronic signal detector 1060. Appropriate electronic signal detectors 1060 are well described in the art. The probe radiation source 1062 may be a Q-switched or mode-locked lasers. The laser may be a diode laser, a solid state laser, an Nd:YAG laser, a gas laser, etc.

A second technique for measuring the stress wave is to observe the change in reflectance pattern from a beam incident on the surface of the skin as shown in FIG. 11. In this configuration, a probe radiation source 1162 generates a probe beam 1163, preferably with a pulse width of between 0.5 and 1000 ns or between 5 and 100 ns, that is absorbed by the skin 1150 to create a stress wave that propagates along the surface of the skin 1150. The probe beam 1163 may pass through an optional probe beam delivery lens 1164 and an optional contact plate 1165 if desired for optical or mechanical purposes such as focusing the probe beam 1163 or mechanically enhancing the propagation of the stress wave. A coherent illumination source 1172 generates a coherent illumination beam 1173 that may be focused or collimated onto the surface of the skin using an optional coherent illumination lens 1174. The coherent illumination beam 1173 is diffracted from the surface of the skin by the stress wave created on the surface of the skin 1150 to create a diffracted beam 1167. The diffracted beam 1167 can be imaged using an imaging lens 1166 onto an imaging detector 1160, such as a CCD camera.

The components 1162, 1163, and 1164 are similar to their analogs in FIG. 10 1062, 1063, and 1064 and can be made from the same components as described above.

The optional contact window 1165 is preferably comprised of a transparent material, such as fused silica or sapphire, through which the probe beam 1163 passes.

The probe beam 1163 is absorbed by the skin 1150 to create a stress wave in the skin 1150. As described above for FIG. 10, the features of the stress wave depend on the optical and mechanical parameters of the skin. Certain features, such as the period and damping of the stress wave, can be evaluated by measuring the diffraction pattern from the diffracted beam 1167 that is imaged on the surface of the imaging detector 1160.

The coherent illumination source 1172 should be a coherent source, for example a HeNe laser. The angle of the coherent illumination beam 1173 relative to the surface of the skin 1150 and the angle of the imaging system relative to the surface of the skin 1150 and relative to the coherent illumination beam 1173 is preferably aligned to maximize the measurement signal. Once a signal has been measured, the decay constant and resonant frequency of the stress wave can be measured with of the apparatii described by FIGS. 10 and 11. DC filtering can also be used to improve the signal to noise ratio of the detected signal.

With the techniques described in FIGS. 10 and 11, preferably, only the first reflected wave is measured and subsequent signals from scattering are temporally filtered. This reduces confusion from multiply reflected waves. This is similar to optical coherence tomography systems in which only the first reflected signal is used. Depending on the particular geometry of the apparatus, this apparatus can be used to measure bulk or localized optical and mechanical properties of the skin, which are changed by the treatment.

The examples presented here have all illustrated the use of these techniques on human skin. This invention is also applicable to treatment of other tissues of the body. For example, puncturing the surface of toenails for treatment of nail fungus, soft palate for treatment of disorders such as sleep apnea and snoring, hair removal, topical delivery of pharmaceuticals or nutriceuticals, or treatment of heart tissue for laser-based TMR treatments can all benefit from the use of this invention.

Although the detailed description contains many specifics, these should not be construed as limiting the scope of the invention but merely as illustrating different examples and aspects of the invention. It should be appreciated that the scope of the invention includes other embodiments not discussed in detail above. For example, in many of the examples above, lasers are used as the embodiment, but these can be generalized to RF, flashlamp, or other electromagnetic energy based treatments as well. Various other modifications, changes and variations which will be apparent to those skilled in the art may be made in the arrangement, operation and details of the method and apparatus of the present invention disclosed herein without departing from the spirit and scope of the invention as defined in the appended claims.

In the specification and in the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. An apparatus for controlled fractional tissue treatment, the apparatus comprising:
    an electromagnetic source that generates electromagnetic energy for creating a fractional treatment;
    a manually movable handpiece that delivers the electromagnetic energy to a target region of human skin;
    a dosage evaluation sensor that measures a skin response to the fractional treatment created by the electromagnetic energy at the target region of human skin; and
    a controller operably connected to the dosage evaluation sensor, the controller configured to automatically adjust in real-time at least one operational parameter of the apparatus in response to the measurements of the dosage evaluation sensor and while delivering the electromagnetic energy to the target region of human skin, and said automatic adjustment controlling the fractional treatment created by the electromagnetic energy.

2. The apparatus of claim 1, wherein the dosage evaluation sensor measures changes in skin birefringence due to the fractional treatment.

3. The apparatus of claim 1, wherein the controller adjusts a spacing of treatment zones or a density of the treatment zones in the fractional treatment if overtreatment or undertreatment is detected by the dosage evaluation sensor.

4. The apparatus of claim 1, wherein the dosage evaluation sensor comprises:
    an ultrasonic transmitter that generates an ultrasonic beam; and
    an ultrasonic receiver that measures characteristic parameters of the ultrasonic beam to quantify changes in the skin response.

5. The apparatus of claim 1, wherein the dosage evaluation sensor measures changes in skin tension or changes in distance between two features located in or on the skin.

6. The apparatus of claim 1, wherein the dosage evaluation sensor uses coherent detection methods.

7. The apparatus of claim 1, wherein the dosage evaluation sensor captures images of the treatment region when illuminated with different wavelength ranges and the images are compared by the dosage evaluation sensor or by the controller.

8. The apparatus of claim 1, wherein the dosage evaluation sensor comprises two sensors that generate data corresponding to the skin condition prior to the fractional treatment or portion thereof and to the skin condition following said fractional treatment or portion thereof.

9. The apparatus of claim 1, wherein the fractional treatment forms a plurality of treatment zones, and a density of the treatment zones is adjusted in response to measurements of the dosage evaluation sensor.

10. The apparatus of claim 1, wherein the dosage evaluation sensor is configured to measure the response to at least one prior treatment pulse to evaluate the appropriate treatment level for at least one subsequent pulse.

11. The apparatus of claim 1, wherein the dosage evaluation sensor captures two or more images formed by different illumination wavelengths.

12. The apparatus of claim 1, wherein the dosage evaluation sensor captures two or more images formed by different polarizations.

13. The apparatus of claim 12, wherein the dosage evaluation sensor detects skin birefringence.

14. The apparatus of claim 1, wherein the dosage evaluation sensor comprises:
- a radiation source configured to generate a stress wave; and
- a detector configured to measure characteristic parameters of the stress wave to quantify changes in the skin response.

15. The apparatus of claim 1, further comprising:
- a positional sensor operably connected to the controller, the positional sensor configured to measure a positional parameter of the handpiece and communicate the at least one positional parameter to the controller.

16. The apparatus of claim 15, wherein the positional parameter is velocity, distance, or position, and the controller is configured to adjust in real-time the at least one operational parameter of the apparatus in response to the measurements of the velocity, the distance, or the position by the positional sensor.

17. The apparatus of claim 15, wherein the controller is configured to adjust in real-time the at least one operational parameter of the apparatus while manually moving the handpiece across the target region of skin.

18. The apparatus of claim 1, wherein the electromagnetic source is a laser configured to generate the electromagnetic energy with a beam size of less than 1 mm for use in creating the fractional treatment.

19. A method for controlled fractional tissue treatment, the method comprising:
- directing electromagnetic energy via a handpiece toward a target region of human skin for creating a fractional treatment;
- manually moving the handpiece across the target region;
- while directing electromagnetic energy toward the target region of human skin, sensing a skin response to the fractional treatment created by the electromagnetic energy at the target region of human skin; and
- automatically adjusting in real-time at least one operational parameter of the electromagnetic energy in response to the sensed skin response, said automatic adjustment controlling the fractional treatment created by the electromagnetic energy.

20. An apparatus for controlled fractional tissue treatment, the apparatus comprising:
- source means for generating electromagnetic energy skin so as to create a fractional treatment;
- manually movable handpiece means for delivering the electromagnetic energy to a target region of human;
- sensor means for measuring a skin response to the fractional treatment created by the electromagnetic energy at the target region of human skin while the handpiece is manually moved relative to the target region and the electromagnetic energy is delivered to the target region of human skin; and
- control means operably connected to the sensor means, said control means for automatically adjusting in real-time at least one operational parameter of the apparatus in response to the measurements of the sensor means and while delivering the electromagnetic energy to the target region of human skin, said automatic adjustment controlling the fractional treatment created by the electromagnetic energy.

* * * * *